(12) United States Patent
Belinky et al.

(10) Patent No.: US 8,691,194 B2
(45) Date of Patent: Apr. 8, 2014

(54) METHODS OF PRODUCING LIGNIN PEROXIDASE AND ITS USE IN SKIN AND HAIR LIGHTENING

(75) Inventors: Paula Belinky, Metulla (IL); Haim Lasser, Kfar Saba (IL); Carlos Dosoretz, Carmiel (IL)

(73) Assignee: R.B.T (Rakuto Bio Technologies) Ltd., Yokneam Ilit (IL)

( * ) Notice: Subject to any disclaimer, the term of this patent is extended or adjusted under 35 U.S.C. 154(b) by 1391 days.

(21) Appl. No.: 12/153,880

(22) Filed: May 27, 2008

(65) Prior Publication Data

US 2009/0041692 A1    Feb. 12, 2009

Related U.S. Application Data

(63) Continuation of application No. 10/538,778, filed as application No. PCT/IL03/01055 on Dec. 11, 2003, now Pat. No. 7,422,734.

(60) Provisional application No. 60/432,678, filed on Dec. 12, 2002.

(51) Int. Cl.
*A61K 8/96* (2006.01)
*C12Q 1/28* (2006.01)
*C12P 1/02* (2006.01)

(52) U.S. Cl.
USPC .............................. 424/62; 435/28; 435/171

(58) Field of Classification Search
USPC ..................................... 424/62; 435/28, 171
See application file for complete search history.

(56) References Cited

U.S. PATENT DOCUMENTS

| | | | |
|---|---|---|---|
| 3,251,742 A | 5/1966 | Soloway | |
| 4,273,760 A * | 6/1981 | Koehler et al. | 424/70.11 |
| 4,830,708 A | 5/1989 | Paice et al. | |
| 5,200,338 A | 4/1993 | Crawford et al. | |
| 5,342,765 A | 8/1994 | Irvine et al. | |
| 5,486,214 A | 1/1996 | Paszczynski et al. | |
| 6,239,093 B1 | 5/2001 | Foley et al. | |
| 6,372,464 B1 | 4/2002 | Yaver et al. | |
| 7,282,067 B2 | 10/2007 | Burgaud et al. | |
| 2002/0115170 A1 | 8/2002 | Yaver et al. | |
| 2006/0051305 A1 | 3/2006 | Belinky et al. | |

FOREIGN PATENT DOCUMENTS

| | | |
|---|---|---|
| CN | 1563369 | 1/2005 |
| EP | 1533371 | 5/2005 |
| EP | 2338896 | 6/2011 |
| GB | 2367995 | 4/2002 |
| JP | 02-072875 | 3/1990 |
| JP | 07-034396 | 2/1995 |
| JP | 07-157409 | 6/1995 |
| JP | 07-165553 | 6/1995 |
| JP | 08-217659 | 8/1996 |
| JP | 2001-122743 | 5/2001 |
| JP | 2002-012535 | 1/2002 |
| KR | 20010114117 | 12/2001 |
| WO | WO 99/15149 | 4/1999 |
| WO | WO 99/60989 | 12/1999 |
| WO | WO 2004/052275 | 6/2004 |

OTHER PUBLICATIONS

Linko et al al. 1993. A Critical Study of Lignin Peroxidase Activity Assay by Veratryl Alcohol Oxidation. Biotechnology Techniques, vol. 7, No. 1, pp. 75-80.*
Farrell et al. 1989.Physical and enzymatic properties of lignin peroxidase isoenzymes from *Phanerochaete chrysosporium*. Enzyme & Microbial Technology, vol. 11, pp. 322-328.*
Response Dated Apr. 13, 2010 to Decision of Rejection of Jan. 5, 2010 From the Japanese Patent Office Re.: Application No. 2004-558336.
Butler et al. "Destruction of Fungal Melanins by Ligninases of *Phanerochaete chrysosporium* and Other White Rot Fungi", International Journal of Plant Science, 159(6):989-995, 1998.
Coll et al. "Purification and Characterization of a Phenoloxidase (Laccase) From the Lignin-Degrading Basidiomycete PM1 (CECT 2971)", Applied and Environmental Microbiology, 59(8): 2607-2613, Aug. 1993.
Glenn et al. "Purification and Characterization of an Extracellular Mn(II)-Dependent Peroxidase From the Lignin-Degrading Basidiomycete, *Phanerochaete chrysosporium*", Archives of Biochemistry and Biophysics, 242(2):329-341, 1985.
Sigma-Aldrich "Peroxidase From Horseradish. Sigma Type VI", Sigma-Aldrich, Catalog No. P8375, Product Description.
Sollewijn Gelpke et al. "Lignin Peroxidase Oxidation of Veratryl Alcohol: Effects of the Mutants H82A, Q222A, W171A, and F267L", Biochemistry, 41(10): 3498-3506, 2002.
Tuisel et al. "Lignin Peroxidase H2 From *Phanerochaete chrysosporium*: Purification, Characterization and Stability to Temperature and pH", Archives of Biochemistry and Biophysics, 279(1): 158-166, May 15, 1990.
Decision of Rejection Dated Jan. 5, 2010 From the Japanese Patent Office Re.: Application No. 2004-558336 and Its Translation Into English.
Response Dated Nov. 5, 2010 to Office Action of Jun. 13, 2010 From the State Intellectual Property Office of the People's Republic of China Re. Application No. 200810108139.2.
Woo et al. "Decolorization of Melanin by Lignin Peroxidase From *Phanerochaete chrysosporium*", Biotechnology and Bioprocess Engineering, 9(4):256-260, 2004.
Bulter "Fungal Melanins: A Review", Canadian Journal of Microbiology, 44(12): 1115-1136, 1998. Abstract.
Communication Pursuant to Article 96(2) EPC Dated Aug. 10, 2006 From the European Patent Office Re.: Application No. 03777155.7.
Supplementary Partial European Search Report Dated Mar. 16, 2006 From the European Patent Office Re.: Application No. 03777155.7.

(Continued)

*Primary Examiner* — Jon P Weber
*Assistant Examiner* — Kailash C Srivastava

(57) ABSTRACT

Methods of producing lignin peroxidase are provided. Also provided are methods and cosmetic compositions suitable for skin and hair lightening as well as kits and an article-of manufacturing including active ingredients for skin and hair lightening.

15 Claims, 11 Drawing Sheets
(9 of 11 Drawing Sheet(s) Filed in Color)

(56) References Cited

OTHER PUBLICATIONS

Communication Pursuant to Article 94(3) EPC Dated May 7, 2008 From the European Patent Office Re.: Application No. 03777155.7.
International Search Report Dated Aug. 26, 2004 From the International Searching Authority Re.: Application No. PCT/IL03/01055.
Supplemental Notice of Allowance Dated Mar. 10, 2008 From the US Patent and Trademark Office Re.: U.S. Appl. No. 10/538,778.
Notice of Allowance Dated Feb. 20, 2008 From the US Patent and Trademark Office Re.: U.S. Appl. No. 10/538,778.
Official Action Dated Sep. 13, 2007 From the US Patent and Trademark Office Re.: U.S. Appl. No. 10/538,778.
Examination Report Dated Apr. 23, 2007 From the Government of India Patent Office Re.: Application No. PCT/IL03/01055.
Examination Report Dated Apr. 4, 2008 From the Government of India Patent Office Re.: Application No. PCT/IL03/01055.
Translation of Notice of Reason For Rejection Dated Aug. 8, 2008 From the Japanese Patent Office Re.: Application No. 2004-558336.
Communication Pursuant to Rules 70(2) and 70a(2) EPC and Reference to Rule 39(1) EPC Dated Sep. 26, 2011 From the European Patent Office Re. Application No. 10176875.2.
Response Dated Nov. 30, 2011 to the Notice of the Reason for Rejection of Aug. 23, 2011 From the Korean Intellectual Property Office Re. Application No. 2005-7010774.
Translation of Office Action Dated Jun. 13, 2010 From the State Intellectual Property Office of the People's Republic of China Re. Application No. 200810108139.2.
Response Dated Jan. 27, 2011 to Notice of the Reason for Rejection of Oct. 25, 2010 From the Korean Intellectual Property Office Re. Application No. 2005-7010774.
Translation of Notice of the Reason for Rejection Dated Oct. 25, 2010 From the Korean Intellectual Property Office Re. Application No. 2005-70110774.
European Search Report and the European Search Opinion Dated Aug. 24, 2011 From the European Patent Office Re. Application No. 10176875.2.
Translation of Notice of Reasons for Rejection Dated Aug. 12, 2011 From the Japanese Patent Office Re. Application No. 2009-2147.
Translation of Notice of the Reason for Rejection Dated Aug. 23, 2011 From the Korean Intellectual Property Office Re. Application No. 2005-7010774.

Dominguez et al. "Amelioration of Ligninolytic Enzyme Production by *Phanerochaete chrysosporium* in Airlift Bioreactors", Biotechnology Letters, 23(6): 451-455, 2001.
Duran et al. "Degradation of Chlorophenols by *Phanerochaete chrysosporium*: Effect of 3,4-Dichlorophenol on Extracellular Peroxidase Activities", Applied Microbiology and Biotechnology, 59(2-3): 284-288, Jun. 1, 2002.
Nakamura et al. "Lignin Peroxidase Production by *Phanerochaete chrysosporium* Immobilized on Polyurethane Foam", Journal of Chemical Engineering of Japan, 30(1): 1-6, 1997.
Odier et al. "Multiple Lignin Peroxidases of *Phanerochaete chrysosporium* INA-12", Enzyme and Microbial Technology, 12(6): 447-452, Jun. 1990.
Rothschild et al. "Ligninolytic System Formation by *Phanerochaete chrysosporium* in Air", Applied and Environmental Microbiology, 61(5): 1833-1838, May 1995.
Communication Pursuant to Article 94(3) EPC Dated Apr. 8, 2008 From the European Patent Office Re.: Application No. 03777155.7.
Communication Pursuant to Rule 95(3) EPC Dated Jun. 21, 2012 From the European Patent Office Re.: Application No. 03777155.7.
Communication Pursuant to Article 94(3) EPC Dated Apr. 19, 2012 From the European Patent Office Re. Application No. 10176875.2.
Translation of Office Action Dated Apr. 12, 2012 From the State Intellectual Property Office of the People's Republic of China Re. Application No. 200810108139.2.
Translation of Notice of Reason for Rejection Dated Aug. 3, 2012 From the Japanese Patent Office Re.: Application No. 2009-2147.
Rothschild et al. "Manganese Deficiency Can Replace High Oxygen Levels Needed for Lignin Peroxidase Formation by *Phanerochaete chrysosporium*", Applied and Environmental Microbiology, 65(2): 483-488, Feb. 1999.
Tonon et al. "Influence of Veratryl Alcohol and Hydrogen Peroxide on Ligninase Activity and Ligninase Production by *Phanerochaete chrysosporium*", Applied and Environmental Microbiology, 54(2): 446-472, Feb. 1988.
Translation of Notice of Reasons for Rejection dated Jun. 14, 2013 From the Japanese Patent Office Re. Application No. 2009-2147.
Examination Report Dated Sep. 23, 2013 From the Government of India, Patent Office, Intellectual Property Building Re. Application No. 2013/CHENP/2008.
Communication Pursuant to Article 94(3) EPC Dated Nov. 27, 2013 From the European Patent Office Re. Application No. 10176875.2.

\* cited by examiner

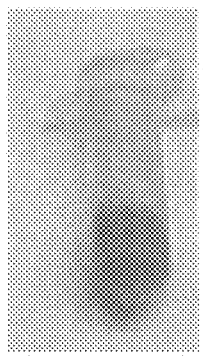 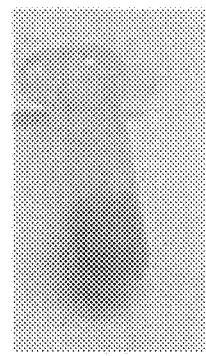
Fig. 8a    Fig. 8b
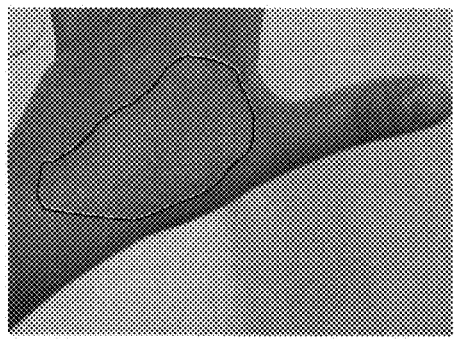 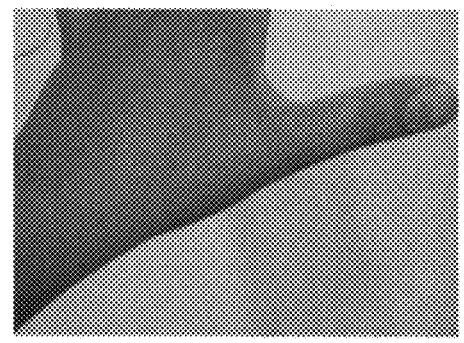
Fig. 9a    Fig. 9b
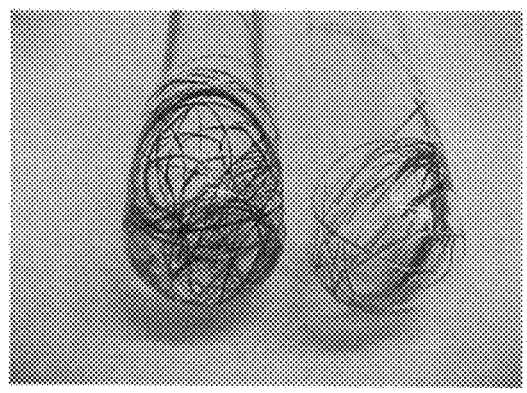
Fig. 10

SEQUENCE LISTING

```
<160> NUMBER OF SEQ ID NOS: 1

<210> SEQ ID NO 1
<211> LENGTH: 1119
<212> TYPE: DNA
<213> ORGANISM: Phanerochaete chrysosporium

<400> SEQUENCE: 1
atggcgttca agcagctcct cgcagccctc tccgtcgccc tgaccctcca ggtcacccaa      60
gctgccccga acctcgacaa gcgcgtcgct tgccccgacg gcgtgcacac cgcctccaac     120
gcggcgtgct gtgcatggtt cccggtcctc gatgatatcc agcagaacct cttccacggt     180
ggccagtgcg gtgccgaggc ccacgaggcc cttcgtatgg tcttccatga ctccatcgct     240
atctcgccca agcttcagtc gcagggcaag tttggcggcg gcggcgcgga cggctcgatc     300
attaccttct cctcgatcga gaccacgtac cacccgaaca tcggcctcga cgaggtcgtc     360
gccatccaga agccgttcat cgcgaagcac ggcgtcacgc gcggcgattt catcgcgttc     420
gccggtgccg tcggcgtgag caactgcccg ggcgcgccgc agatgcagtt cttcctcggc     480
cgccccgagg cgacgcaggc cgccccgac ggtctcgtgc ccgagccctt ccacaccatc     540
```

-continued

```
gatcaggttc tcgctcgcat gcttgatgct ggtggcttcg acgagatcga gactgtctgg      600
ctgctctctg cccactccat cgcggctgcg aacgacgtcg acccgaccat ctccggcctg      660
ccgttcgact ccacccctgg ccagttcgac tcccagttct tcgtcgagac gcagctccgc      720
ggtaccgcat tccctggcaa gactggtatc cagggcaccg tcatgtcccc gctcaagggc      780
gagatgcgtc tgcagacgga ccacttgttc gcgcgcgact cgcgcacggc gtgcgagtgg      840
cagtccttcg tcaacaacca gacgaagctg caggaggact tccagttcat cttcacggcg      900
ctctcgaccc tcggccacga catgaacgcc atgaccgact gctccgaggt catccccgcg      960
cccaagcccg tcaacttcgg cccgtcgttc ttccccgccg gtaagacgca cgccgacatc      1020
gagcaggcct gcgcatccac gccgttcccg acgctcatca ccgcccccgg tccctctgcg      1080
tccgtcgctc gcatccccccc gccgccgtcc cccaactaa                             1119
```

METHODS OF PRODUCING LIGNIN PEROXIDASE AND ITS USE IN SKIN AND HAIR LIGHTENING

RELATED APPLICATIONS

This application is a continuation of U.S. patent application Ser. No. 10/538,778 filed on Jun. 10, 2005, now U.S. Pat. No. 7,422,734 which is a National Phase of PCT Patent Application No. PCT/IL03/01055 having International Filing Date of Dec. 11, 2003, which claims the benefit of U.S. Provisional Patent Application No. 60/432,678 filed on Dec. 12, 2002.

FIELD AND BACKGROUND OF THE INVENTION

The present invention relates to methods of producing lignin peroxidase and its use in skin and hair lightening.
Melanin The color of human skin and hair is governed by the quantity, quality, and distribution of melanin, a pigment which is also present in plants and microorganisms.

The synthesis of melanin initiates from the precursor L-tyrosine which is transformed into a second precursor dopaquinone via the action of tyrosinase. In the biosynthesis of mammalian melanin this intermediate may be polymerized via two major pathways (FIG. 1). Intramolecular nucleophilic addition of the amino group gives rise to the indole derivative leucodopachrome which, following polymerization, yields the dark brown to black pigment eumelanin. In the presence of thiol compounds thioesther derivatives of dopa are formed; the reaction with cysteine yields cysteinyldopa, which following further oxidation and polymerization yields the yellow to redish brown pigment phaeomelanin. Consequently, eumelanin is mainly composed of 5,6-dihydroxyindole (DHI) and 5,6-dihydroxyindole-2-carboxylic acid (DHICA) units, whereas phaeomelanin mainly contains benzothiazine units (Alaluf et al., 2001). The availability and mutual ratio of these two pigments influences the chemical composition of the polymeric pigment.

Synthesis of melanin takes place in granules, which are referred to as melanosomes (Cooksey et al., 1997) which are present in melanocyte cells present in the epidermal basal layer; synthesis of melanin in these cells is induced by ultraviolet (UV) light. Following synthesis, melanin migrates to epidermal cells and is dispersed therein, where melanin is decolored following dermal metabolism and then scaled off in the form of dirt at the time of skin renewal. Melanin has a clinical importance since it protects the skin from adverse effects caused by UV light. However, high levels of melanin can result in unwanted skin and hair darkening, while the heterogeneous distribution thereof can lead to chloasma and freckling which can be aesthetically displeasing.
Lightening Products Skin lightening products have become increasingly popular in the past few years. The main purpose of skin lightening products is to lighten or whiten the skin or to treat pigmentation disorders such as chloasma, freckles, pregnancy marks and age spots. Several types of skin lightening products are presently available.

Products based on the degeneration and death of pigment cells typically include harsh chemicals, such as hydroquinone, 4-isopropylcatechol, and hydroquinone monobenzyl ether, that promote skin whitening and skin lightening or fade out skin pigmentation. Such products are typically inefficient and may be harmful to the skin since a continuous external application of these products can lead to permanent leucoderma and side effects such as dyschromatosis and rash.

Other lightening products are based on the inhibition of tyrosinase, the enzyme that transforms the precursor L-tyrosine into a second precursor dopaquinone. This group of products includes Arbutin, a glucose hydroquinone compound which is capable of inhibiting tyrosinase by chelating copper ions thereby suppressing the tautomerization from Dopachrome to DHICA.

Melanostat is another lightening product that acts through tyrosinase. Melanostat is a synthetic peptide that functions in deactivating melanogenesis in melanocytes. Several antioxidant compounds that can inhibit the production of melanin are also utilized in lightening products. Since the synthesis of melanin involves an oxidation reaction, blocking the oxidation at various points from tyrosine/DOPA to melanin ultimately inhibits the synthesis of melanin.

One antioxidant which is utilized to block melanin synthesis is (Vitamin C) which acts as a reducing agent on melanin intermediates and blocks oxidative reactions; other antioxidants utilized by lightening products include bioflavonoids which are typically extracted from mulberry or licorice.

Hair lightening products act on the melanin inside the hair cortex. There are several chemicals that can lighten hair, among these are included hydrochloric acid, sodium hypochlorite and hydrogen peroxide.

The most commonly used chemical for lightening hair is hydrogen peroxide. To maintain desired effectiveness, solutions of hydrogen peroxide must be stabilized using compounds such as acetanilide, dilute acids, colloidal silica, p-hydroxybenzoates, oxyquinoline sulfate, phenacetin, and tin compounds (sodium stannate, stannic hydroxide, stannous octoate). Before hair is lightened, ammonia is added to the hydrogen peroxide solution to enhance penetration of hydrogen peroxide through the cuticle, the outer layer of the hair, and to thus accelerate the oxidation reaction.

While reducing the present invention to practice, the present inventors have uncovered that Lignin peroxidase isoenzyme H1 can oxidize melanin in vitro and can further lighten skin and hair in vivo.

Thus, the present invention provides cosmetic compositions and methods which are highly suitable for skin and hair lightening.

SUMMARY OF THE INVENTION

According to one aspect of the present invention there is provided a method of lightening a skin region or hair of a subject, comprising applying to the skin region or hair at least one type of a lignin modifying enzyme in a manner suitable for oxidizing a pigment contained within cells of the skin region or hair.

According to another aspect of the present invention there is provided a cosmetic composition for lightening a skin region or hair of a subject comprising at least one type of a lignin modifying enzyme and a cosmetically acceptable carrier.

According to yet another aspect of the present invention there is provided a kit for lightening a skin region or hair comprising a first container including a lignin modifying enzyme, and a second container including an electron acceptor.

According to still another aspect of the present invention there is provided an article-of-manufacturing comprising packaging material and a cosmetic composition identified for lightening a skin region or hair of a subject being contained within the packaging material, the cosmetic composition including, as an active ingredient, a lignin modifying enzyme, and a cosmetically acceptable carrier.

According to further features in preferred embodiments of the invention described below, the method is effected via a topical application of a preparation including at least one type of lignin modifying enzyme.

According to still further features in the described preferred embodiments the method is effected via intradermal or subcutaneous administration of a preparation including at least one type of lignin modifying enzyme.

According to still further features in the described preferred embodiments the lignin modifying enzyme is included in a composition formulated for skin or hair application.

According to still further features in the preferred embodiments of the invention described below, the lignin modifying enzyme is lignin peroxidase.

According to still further features in the described preferred embodiments the lignin peroxidase is isoenzyme H1 or a modified form of isoenzyme H2.

According to still further features in the described preferred embodiments the cosmetic composition further comprises an electron acceptor.

According to still further features in the described preferred embodiments the electron acceptor is hydrogen peroxide.

According to still further features in the described preferred embodiments the cosmetic composition further comprises veratryl alcohol.

According to still further features in the described preferred embodiments the composition comprises at least one type of an epidermal penetrant.

According to still further features in the described preferred embodiments the composition comprises at least one type of a hair penetrant.

According to still further features in the described preferred embodiments the method is effected for a time period selected according to a level of lightening desired.

According to still further features in the described preferred embodiments the cosmetically acceptable carrier includes transcutol and/or butylene glycol.

According to still further features in the described preferred embodiments the cosmetically acceptable carrier includes alkanol amines.

According to still further features in the described preferred embodiments the lignin peroxidase in the cosmetic composition is provided at a concentration of at least 1 U/gr.

According to still further features in the described preferred embodiments the hydrogen peroxide in the cosmetic composition is provided at a concentration of at least 0.005%.

According to still further features in the described preferred embodiments the veratryl alcohol in the cosmetic composition is provided at a concentration of at least 0.05%.

According to still further features in the described preferred embodiments the first container of the kit for lightening a skin region or hair further comprises veratryl alcohol.

According to still further features in the described preferred embodiments the first and/or second container(s) of the kit for lightening a skin region or hair further include a cosmetically acceptable carrier suitable for epidermal penetration.

According to still further features in the described preferred embodiments the first and/or second container(s) of the kit for lightening a skin region or hair further include a cosmetically acceptable carrier suitable for hair penetration.

According to an additional aspect of the present invention there is provided a method of lightening a skin region of a subject, the method comprising, expressing within cells of the skin region a lignin modifying enzyme in a manner suitable for oxidizing a pigment contained within cells of the skin region.

According to still further features in the described preferred embodiments the method further comprising a step of providing to the cells of the skin region an electron acceptor.

According to still further features in the described preferred embodiments the electron acceptor is hydrogen peroxide.

According to still further features in the described preferred embodiments the method further comprising a step of providing to the cells of the skin region veratryl alcohol.

According to still further features in the described preferred embodiments expressing is effected by introducing into the cells an expression vector capable of expressing the lignin modifying enzyme.

According to still further features in the described preferred embodiments the vector is a viral vector.

According to still further features in the described preferred embodiments the vector comprises a promoter functionally linked to a lignin modifying enzyme coding sequence.

According to still further features in the described preferred embodiments the lignin modifying enzyme is lignin peroxidase.

According to still further features in the described preferred embodiments the lignin peroxidase is encoded by the polynucleotide sequence set forth in NO:1.

According to an additional aspect of the present invention there is provided a method of producing a lignin peroxidase comprising: (a) culturing *Phanerochaete chrysosporium* fungus on a porous matrix in a stirred and aerated culture medium containing glycerol for a predetermined time period; (b) following the predetermined time period extracting a soluble fraction from the *Phanerochaete chrysosporium* fungus to thereby produce the lignin peroxidase.

According to still further features in the described preferred embodiments the culture medium is devoid of manganese ions.

According to still further features in the described preferred embodiments the aerated culture is obtained by subjecting the culture medium to an aeration rate in the range of 0.1-1 liter per liter per minute.

According to still further features in the described preferred embodiments the culturing is effected at a temperature of 37° C.

According to still further features in the described preferred embodiments the stirred culture medium is obtained by stirring the culture medium at a speed in the range of 50-300 rpm.

According to still further features in the described preferred embodiments the stirred culture medium is obtained by stirring the culture medium at a speed of 100 rpm.

According to still further features in the described preferred embodiments the predetermined time period is selected from the range of 3-10 days.

According to still further features in the described preferred embodiments the predetermined time period is 7 days.

According to still further features in the described preferred embodiments the glycerol is provided at a concentration range of 3-20 grams per liter.

According to still further features in the described preferred embodiments the glycerol is provided at a concentration of 6 grams per liter.

According to still further features in the described preferred embodiments the culture medium further includes veratryl alcohol.

According to still further features in the described preferred embodiments the veratryl alcohol is provided at a concentration range of 0.5-4 mM.

According to still further features in the described preferred embodiments the veratryl alcohol is provided at a concentration of 2 mM.

According to still further features in the described preferred embodiments the lignin peroxidase is isoenzyme H1 or a modified form of isoenzyme H2.

According to still further features in the described preferred embodiments the porous matrix is a polyurethane foam.

According to yet an additional aspect of the present invention there is provided an aqueous extract of *Phanerochaete chrysosporium* fungus exhibiting lignin peroxidase enzymatic activity in the range of 500-2000 units per liter.

According to still further features in the described preferred embodiments the lignin peroxidase activity is 1500 units per liter.

According to still further features in the described preferred embodiments the lignin peroxidase enzymatic activity is isoenzyme H1 or a modified form of isoenzyme H2.

The present invention successfully addresses the shortcomings of the presently known configurations by providing efficient methods and compositions for lightening a skin region or hair of a subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a prior art schematic illustration of the biosynthesis of mammalian melanin adopted from Alaluf et al., 2001.

FIG. 2 is a color photograph that illustrates the stirred tank reactor (STR) for the production of lignin peroxidase by *Phanerochaete chrysosporium* immobilized on polyurethane foam.

Figure 3:
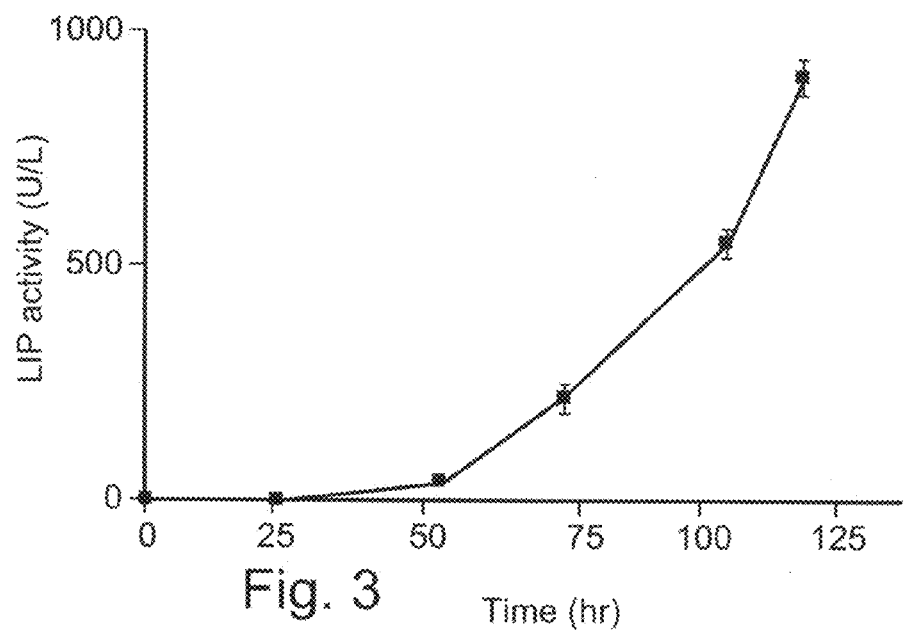

FIG. 3 is a line drawing that illustrates LIP activity in a fermentor culture of *P. chrysosporium* as a function of culture age. *P. chrysosporium* was grown in an STR fermentor as described in Example 1 of the Examples section and LIP activity was assayed in the extracellular fluid by following the oxidation of veratryl alcohol to veratryl aldehyde as described in Examples. Error bars represent standard deviations of 3 replicate experiments.

Figure 4:
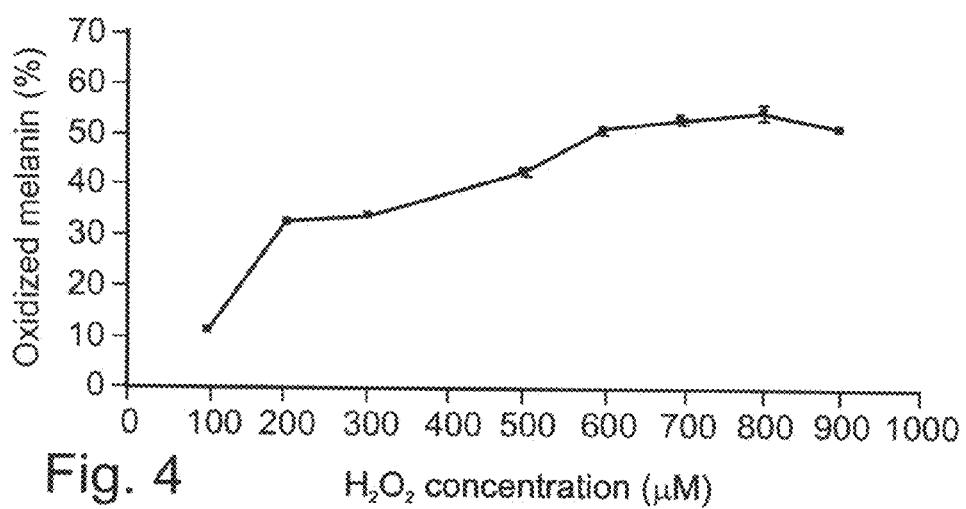

FIG. 4 is a line drawing that illustrates the oxidation of melanin, at an initial concentration of 70.5 μg/ml, by LIP (0.48 μM) as a function of increasing concentrations of hydrogen peroxide in the presence of 1.5 mM veratryl alcohol in 50 mM tartrate buffer, at pH 3.5. Oxidation of melanin was determined by measuring its absorbance at 460 nm, at the beginning of the enzymatic reaction and after 160 seconds, and the percentages of oxidized melanin were calculated. The error bars represent standard deviations of 3 replicate experiments.

Figure 5:
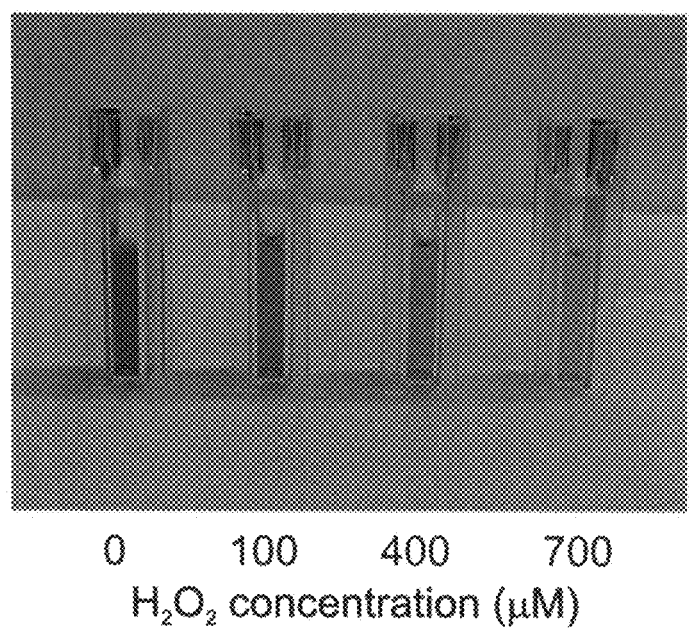

FIG. 5 is a color photograph that illustrates the effect of increasing concentrations of hydrogen peroxide on the oxidation of melanin by LIP. Degree of oxidation of melanin is visualized by decrease in color intensity in comparison to the enzymatic reaction without the inclusion of hydrogen peroxide (0 μM). Numbers below the picture indicate concentrations of $H_2O_2$ expressed in μM.

Figure 6:
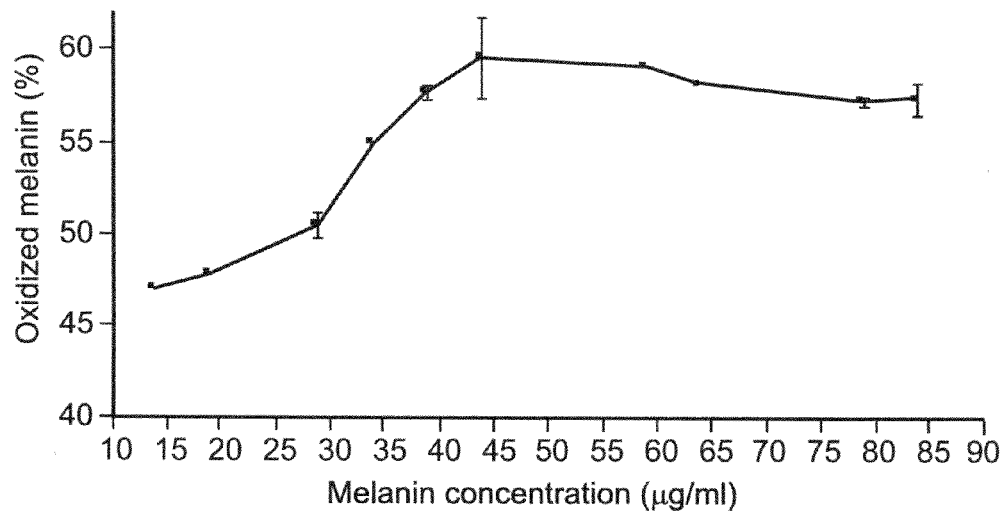

FIG. 6 is a line drawing that illustrates the degree of oxidation of different concentrations of melanin by LIP (0.48 μM) in 50 mM tartarate buffer at pH 3.5 in the presence of veratryl alcohol (1.5 mM) and hydrogen peroxide (600 μM). Error bars represent standard deviations of 3 replicate experiments.

Figure 7:
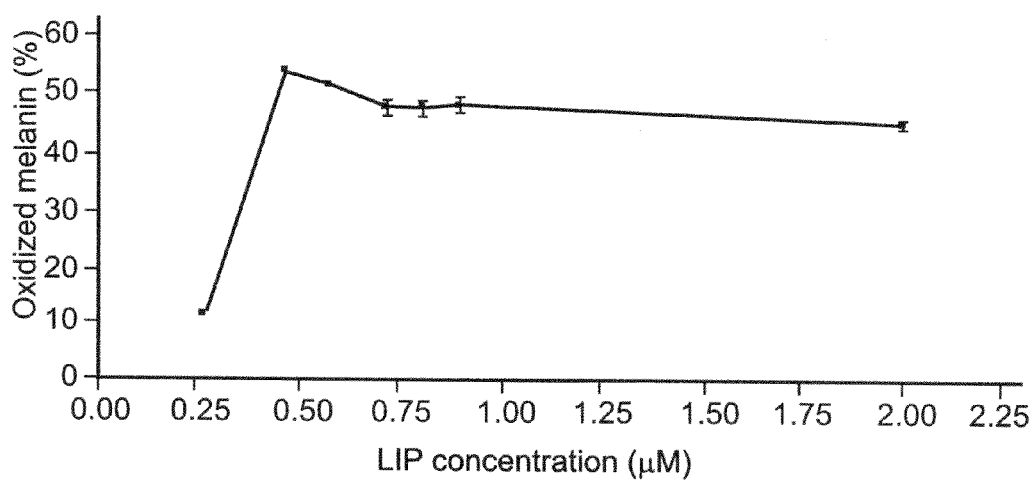

FIG. 7 is a line drawing that illustrates the degree of oxidation of melanin as a function of LIP concentrations. Oxidation of melanin (70 μg/ml) was performed by increasing concentrations of LIP in the presence of veratryl alcohol (1.5 mM) and hydrogen peroxide (700 μM) in 50 mM tartrate buffer at pH 3.5. Error bars represent standard deviations of 3 replicate experiments.

FIGS. 8a-b are color photographs that illustrate visualization of the oxidation of melanin by LIP when used in a cream formulation. Decolorization of melanin is observed after the addition of the activator cream to the LIP cream (FIG. 8b) but not in the presence of the LIP cream alone (FIG. 8a).

FIGS. 9a-b are color photographs that illustrate the effect of LIP cream on skin whitening. Shown is a photograph of a woman's hand taken one week following the application of LIP (twice daily) in a cream formulation. The area treated with LIP (FIG. 9a, circled in black) is much lighter than the rest of the skin in the hand (FIG. 9b).

FIG. 10 is a color photograph that illustrates the effect of LIP on hair bleaching in vivo. A woman's hair was soaked for 1 hr in 50 mM carbonate buffer at pH 11.5. The hair was pre-incubated for 10 seconds with 25 U of LIP and immersed for 1 hr in tartarate buffer at pH 3.5 with veratryl alcohol (1.5 mM) and hydrogen peroxide (8.8 mM). A significant lightening effect was observed in the hair treated with LIP (FIG. 10, right tube) as compared with the hair treated with the same solution without LIP (FIG. 10, left tube).

Figure 11A:
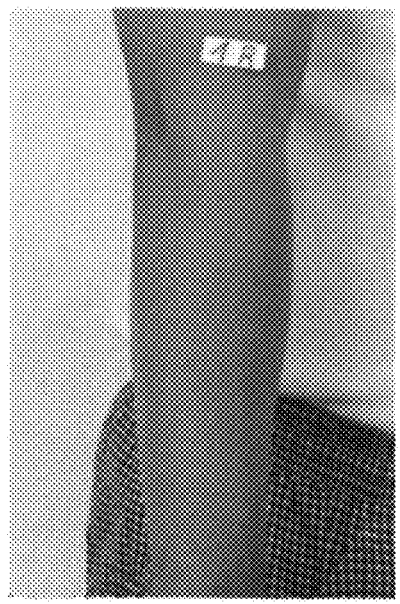
Figure 11B:
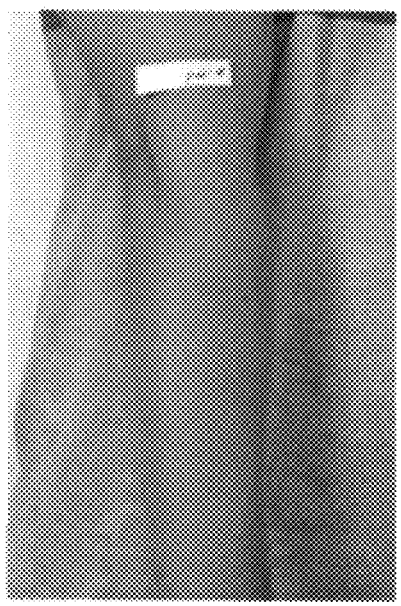

FIGs. 11a-b are color photographs of the right forearm of study subject No. 1 illustrating the effect of the LIP whitening cream on skin pigmentation. FIG. 11a - a photograph taken at day 0; FIG. 11b - a photograph taken at day 21.

Figure 12A:
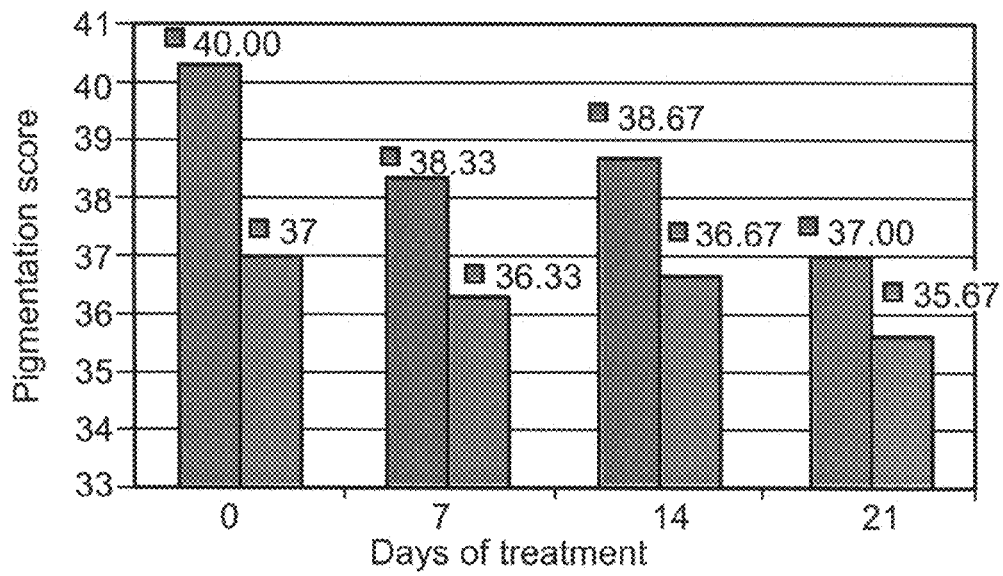
Figure 12B:
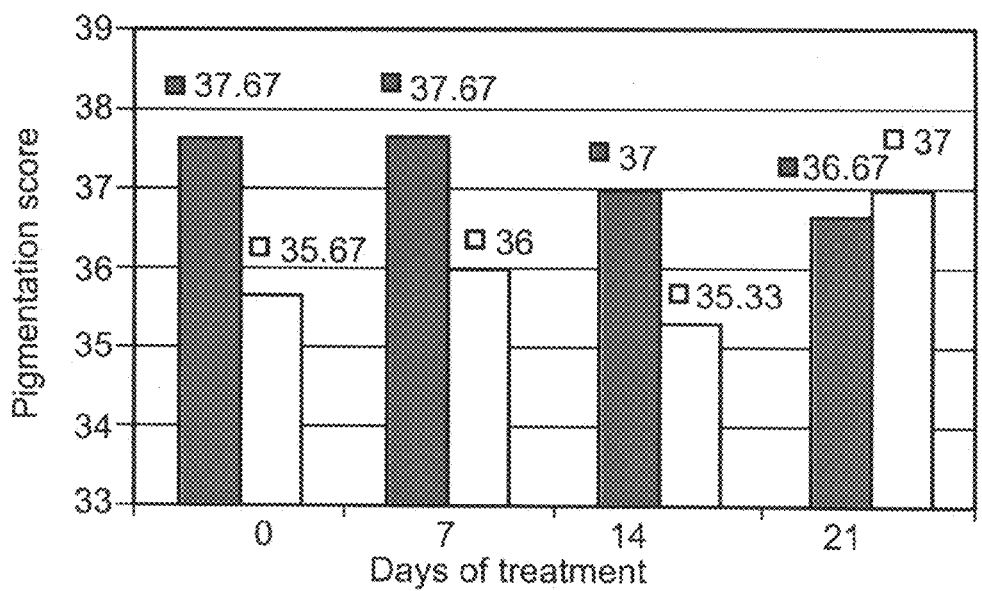
Figure 12C:
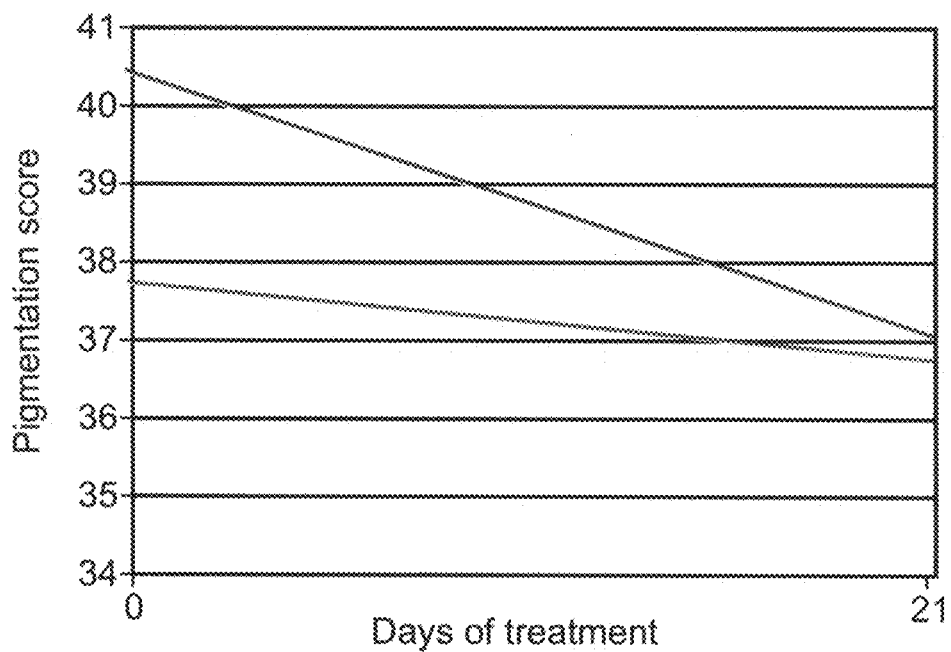

FIGS. 12a-c are bar graphs that illustrate the effect of LIP or Hydroquinone creams on skin whitening in study subject No. 1. The LIP or Hydroquinone creams were applied in the upper parts of the right and left forearms while the lower parts remained untreated. The degree of skin pigmentation was measured in both forearms in intervals of 7 days using the Derma Spectrometer. FIG. 12a - application of LIP cream; FIG. 12b - application of Hydroquinone cream; blue columns =upper part of the right forearm treated with the LIP cream; light blue columns =untreated lower part of right forearm; pink columns =upper part of the left forearm treated with Hydroquinone; white columns =untreated lower part of the left forearm; FIG. 12c is a line graph comparing the decrease in skin pigmentation in the upper forearms following 21 days of treatment using the LIP cream (FIG. 12c, blue line) or the Hydroquinone cream (FIG. 12c, pink line). Note the sharp decrease in skin pigmentation following 21 days of treatment using the LIP cream as compared with the moderate decrease using the Hydroquinone cream.

Figures 13A, 13B:
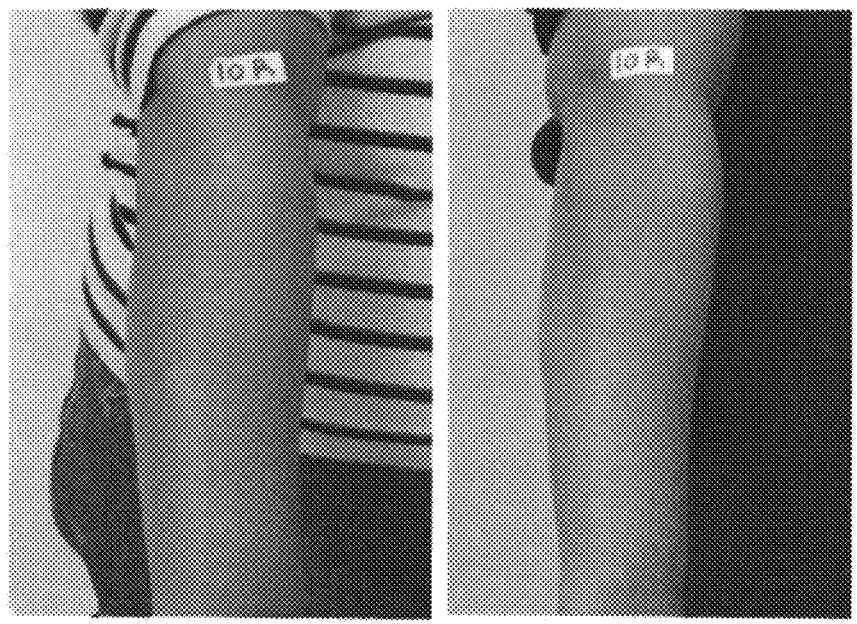

FIGS. 13a-b are color photographs of the right forearm of study subject No. 10 illustrating the effect of the LIP whitening cream on skin pigmentation. FIG. 13a a photograph taken at day 0; FIG. 13b - a photograph taken at day 21.

Figure 14A:
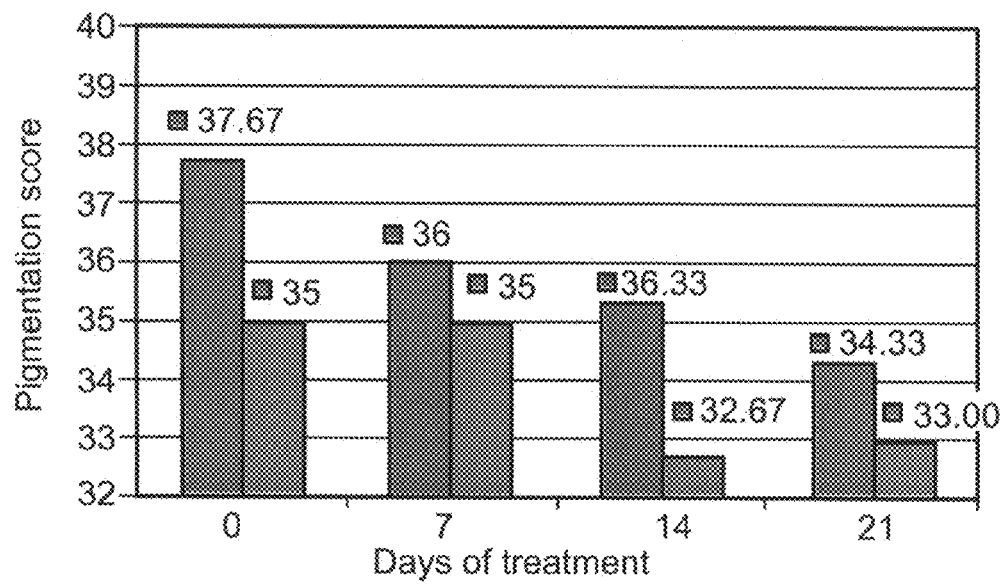
Figure 14B:
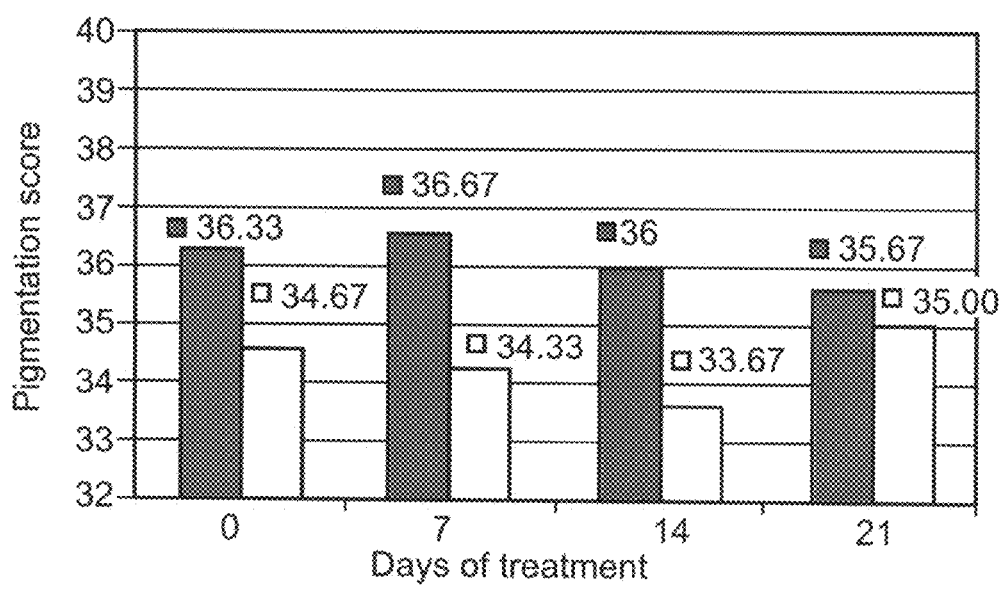
Figure 14C:
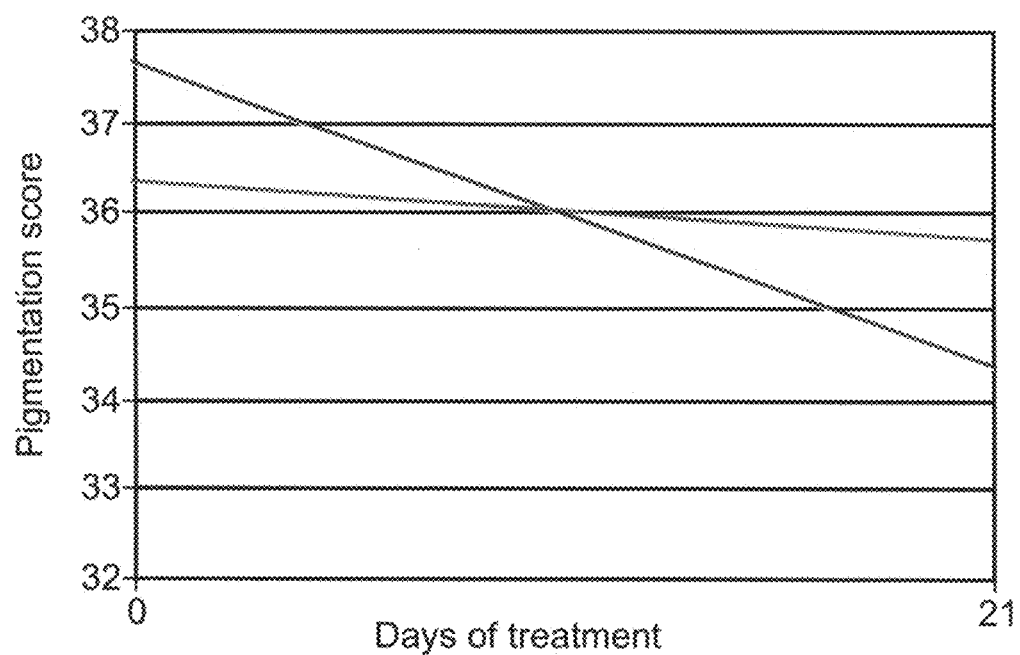

FIGS. 14a-c are bar graphs that illustrate the effect of LIP or Hydroquinone creams on skin whitening in study subject No. 10. The LIP or Hydroquinone creams were applied in the upper parts of the right and left forearms while the lower parts remained untreated. The degree of skin pigmentation was measured in both forearms in intervals of 7 days using the Derma Spectrometer. FIG. 14a - application of LIP cream; FIG. 14b - application of Hydroquinone cream; blue columns =upper part of the right forearm treated with the LIP cream; light blue columns =untreated lower part of right forearm; pink columns =upper part of the left forearm treated with Hydroquinone; white columns =untreated lower part of the left forearm; FIG. 14c is a line graph comparing the decrease in skin pigmentation in the upper forearms following 21 days of treatment using the LIP cream (FIG. 14c, blue line) or the Hydroquinone cream (FIG. 14c, pink line). Note the sharp decrease in skin pigmentation following 21 days of treatment using the LIP cream as compared with the moderate decrease using the Hydroquinone cream.

Figure 15A:
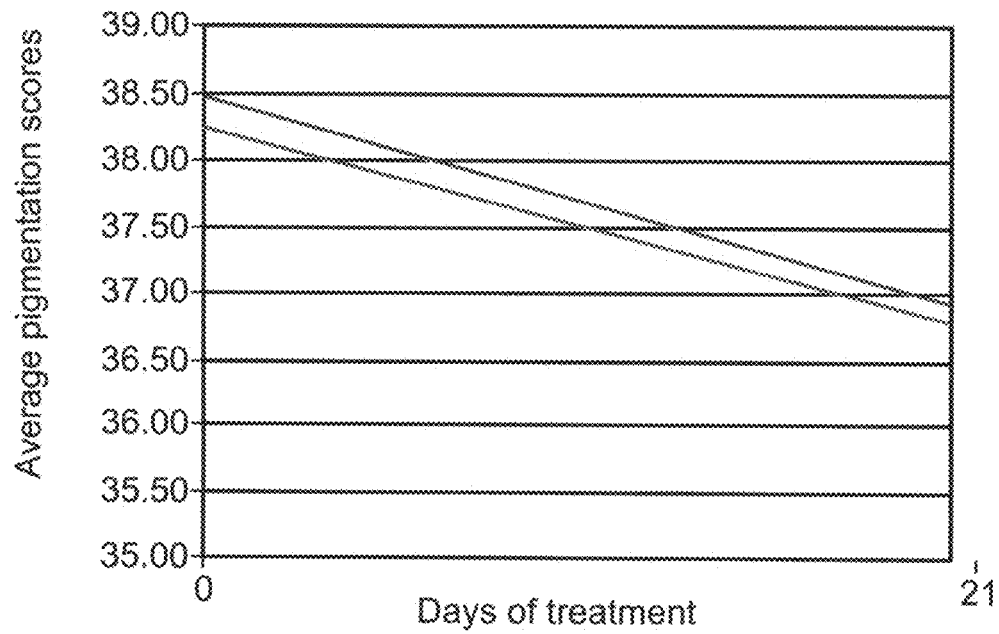
Figure 15B:
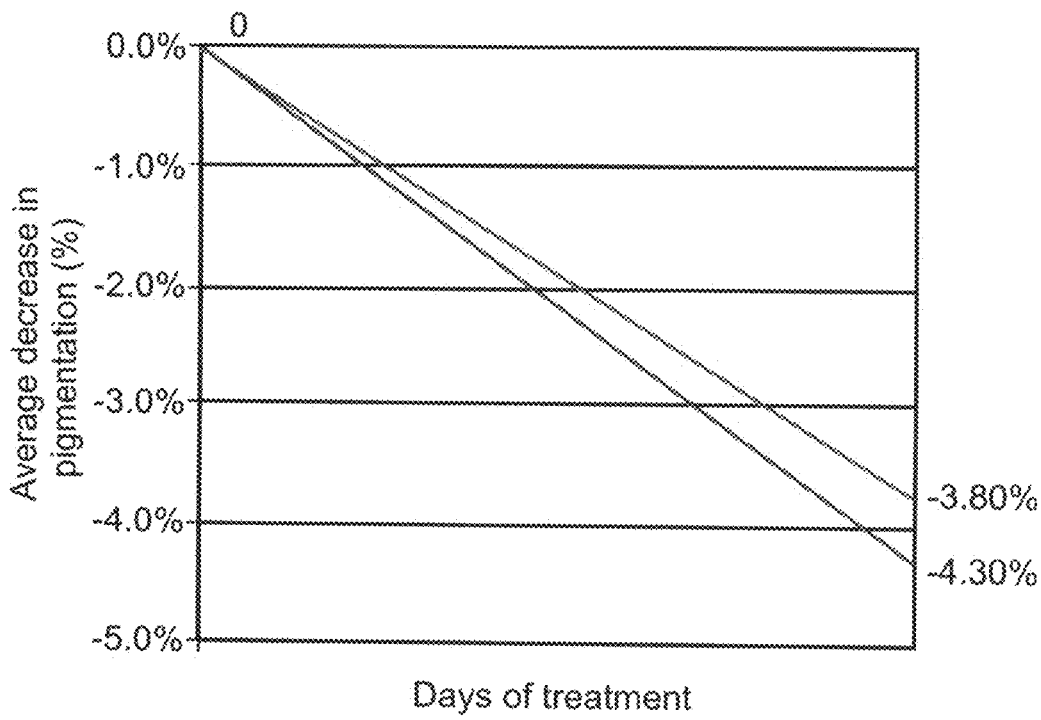

FIGS. 15a-b are line graphs illustrating the average effect of the LIP and Hydroquinone creams on skin whitening in all 12 study subjects. FIG. 15a - the average pigmentation scores; FIG. 15b - the average decrease in pigmentation as a fraction of the initial pigmentation score.

DESCRIPTION OF THE PREFERRED EMBODIMENTS

The present invention is of methods and cosmetic compositions which can be used for lightening a skin region or hair of a subject.

Particularly, the methods of the present invention can be used for treating uneven skin complexions which result from hyperpigmentation-related medical conditions such as melasma, chloasma, age spots, freckles, ochronosis, and lentigo.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The degree of skin pigmentation is a source of concern among the general population. Some people suffer from age spots and pregnancy marks and wish such pigmented spots to be less pronounced. Other people have freckles, chloasma, melasma, ochronosis and lentigo that are usually treated with skin lightening products that lighten and smoothen the pigmentation of the skin. However, current skin lightening products are either harsh chemicals such as hydroquinone that can lead to permanent leucoderma and side effects such as dyschromatosis and rash, or are not efficient enough in lightening the skin. Among them are the products based on the inhibition of the tyrosinase, the enzyme that transforms the precursor L-tyrosine into a second precursor dopaquinone and therefore inhibit the biosynthesis of melanin. Other products are designed to block the oxidation reactions at various points from tyrosine/DOPA to melanin and ultimately inhibit the synthesis of melanin. The latter group of products includes antioxidants such as (Vitamin C) and bioflavonoids.

Hair lightening products utilize high concentrations of hydrogen peroxide in conjunction with ammonia. These products might be a source of discomfort to the treated subject.

As is clearly illustrated in the Examples section which follows, the present inventors have uncovered that lignin peroxidase, and in particular its H1 isoform, can efficiently oxidize melanin and thus can be utilized to lighten skin or hair of a subject.

Although U.S. Pat. No. 5,578,296 identified a melanin decomposing potency in the Basidiomycetes fungus and suggested the use of this fungus to treat chloasma and freckling, to date, the specific enzyme responsible for the melanin decomposition in the fungus has not been uncovered.

Thus according to one aspect of the present invention there is provided a method of lightening a skin region or hair of a subject.

The method according to this aspect of the present invention is effected by applying to the skin region or hair of the subject at least one type of a lignin modifying enzyme in a manner suitable for oxidizing a pigment (e.g., melanin) contained within cells of the skin region or hair.

As used herein, the phrase "lightening a skin region or hair" refers to reducing the tone or color of skin or hair by reducing the pigmentive quality or concentration of melanin pigment contained therein.

As used herein, the phrase "subject" refers to mammals, typically human beings, and preferably those having excess skin or hair pigmentation, or skin imperfections such as freckles etc.

The lignin modifying enzyme utilized by the present invention is preferably lignin peroxidase, which plays a major role in lignin degradation. The active site amino sequence of this lignin modifying peroxidase and the mechanism by which it oxidizes substrates is similar to that of horseradish peroxidase (HRP) and soybean peroxidase (SBP). Lignin modifying peroxidases are able to catalyze the oxidation of substrates with high redox potential. This unique ability is consistent with a heme active site of low electron density, which is indicated by high redox potential [Cai and Tien (1993). J Biotechnol 30: 79-90].

Although any isoforms of lignin peroxidase known in the art can be utilized by the present invention (Rothschild et al., 1997, Appl. Environ. Microbiol. 63: 857-861), the present invention preferably utilizes the H1 isoform, since as is illustrated in the Examples section which follows, this isoform exhibited melanin oxidation activities both in vitro and in vivo.

Several approaches can be used to prepare the lignin modifying enzyme utilized by the present invention.

For example, lignin peroxidase isoenzyme H1 can be prepared from the fungus *Phanerochaete chrysosporium*. High levels of enzymatic activity of lignin peroxidase can be produced from the above fungus when grown in a stirred tank reactor (STR) fermentor while being immobilized on polyurethane foam or in suspension (Dosoretz et al., 1993, Appl Environ Microbiol. 59: 1919-26).

According to preferred embodiments of the present invention the fermentor is connected to a cooling system to maintain a culturing temperature of 37° C. and is stirred at speed of 50-300 rpm, more preferably, 100-200 rpm, most preferably at 160 rpm. In order to increase the yield of lignin peroxidase activity the fermentor is aerated at an aeration rate of 0.1-1 liter of air per liter of culture medium per minutes. According to presently preferred configurations the fermentor is aerated at an aeration rate of 0.2 liter of air per liter of culture medium per minute.

As is described under Materials and Experimental Methods of the Examples section which follows the *Phanerochaete chrysosporium* is cultured under culturing conditions devoid of manganese ions and containing glycerol as a source of carbon. Preferably, the glycerol of the present invention is provided at a concentration range of 3-20 grams per liter. According to presently preferred configurations the glycerol is provided at a concentration of 6 grams per liter.

During the purification process of lignin peroxidase isoenzyme H1 from the above fungus the enzymatic activity of the purified protein is further tested by a change in absorbance at 310 nm that occurs due to the oxidation of veratryl alcohol to veratryl aldehyde.

Since lignin peroxidase isoenzyme H1 can result from a post-translational de-phosphorylation of isoenzme H2 (Kuan and Tien, 1989), the lignin peroxidase used by the present invention can be prepared by dephosphorylating the lignin peroxidase isoenzyme H2.

Lignin modifying enzymes used by the present invention can also be extracted from bacterial cells modified to express the lignin modifying enzyme as disclosed in U.S. Pat. No. 5,200,338. For example, a bacterial cell, such as, *E. coli*, can be transformed with an expression vector including the LIP coding sequence (SEQ ID NO:1) positioned under the regulatory control of a strong constitutive promoter (e.g., SP6). Following expression, the bacterial cells can be lysed and the LIP can be collected using chromatographic techniques (see, Billman-Jacobe, 1996, Curr. Opin. Biotechnol. 7: 500-4; Harris and Emtage, 1986, Microbiol. Sci. 3: 28-31, for further details).

Lignin modifying enzymes used by the present invention can also be extracted from mammalian cell lines such as HeLa cells. In this case the LIP coding sequence is positioned under a strong mammalian promoter (e.g., CMV) in a suitable expression vector (e.g., pCDNA3.1, Invitrogen Life Technologies, Frederick, Md., USA). Following transfection of HeLa cells with the expression vector, the LIP expression product can be extracted from the cells or medium (e.g., by modifying the LIP sequence to include a secretion signal) by conventional purification and chromatography techniques (see Cunha and Aires-Barros, 2002. Mol. Biotechnol. 20: 29-40 for further details).

Although the lignin modifying enzyme can be applied to the skin or hair without necessitating co-application of additional compounds, the lightening capability of the lignin modifying enzyme LIP is enhanced when it is applied in the presence of an electron acceptor (i.e. a molecule capable of oxidizing a substrate), that serves as the oxidizing activator, and/or in the presence of phenolic compounds, such as veratryl alcohol (Harvey et al., 1992, Biochem Soc Trans 20: 345-9), and veratrole that serve as the oxidizing mediators (Ward et al., Enzyme and Microbial Technology (2002), 30: 490-498).

Thus, according to a preferred embodiment of the present invention, the lignin modifying enzyme is applied with prior, concomitant or subsequent application of an oxidizing activator, such as hydrogen peroxide and an oxidizing mediator, such as, veratryl alcohol.

The lignin modifying enzyme can be applied to the skin or hair per se, however, in order to increase lightening efficiency, the lignin modifying enzyme is preferably included in a cosmetic composition which is formulated for specific use, such as, for example, general skin lightening, freckle lightening or hair lightening. These cosmetic compositions may include epidermal penetrants such as butylene glycol and transcutol, and hair penetrants such as alkanol amines.

As used herein a "cosmetic composition" refers to a preparation which includes the active ingredients described hereinabove (e.g., LIP) and additional chemical components such as physiologically suitable carriers and excipients, an oxidizing activator and/or an oxidizing mediator. The purpose of a cosmetic composition is to facilitate administration of the active ingredient to an organism.

Hereinafter, the phrases "suitable carrier" used refer to a carrier or a diluent that does not cause significant irritation to an organism and does not abrogate the biological activity and properties of the lignin modifying enzyme.

Herein the term "excipient" refers to an inert substance added to a cosmetic composition to further facilitate administration of an active ingredient. Examples, without limitation, of excipients include calcium carbonate, calcium phosphate, various sugars and types of starch, cellulose derivatives, gelatin, vegetable oils and polyethylene glycols.

The cosmetic composition may be applied in a local manner, for example, via administration of the cosmetic composition directly into a tissue region of a patient. Suitable routes of administration may, for example, include topical, subcutaneous and intradermal injections.

Cosmetic compositions of the present invention may be manufactured by processes well known in the art, e.g., by means of conventional mixing, dissolving, granulating, dragee-making, levigating, emulsifying, encapsulating, entrapping or lyophilizing processes.

Cosmetic compositions for use in accordance with the present invention thus may be formulated in conventional manner using one or more physiologically acceptable carriers comprising excipients and auxiliaries, which facilitate processing of the active ingredients into preparations. Proper formulation is dependent upon the administration approach chosen.

For injection, the active ingredients of the cosmetic composition may be formulated in aqueous solutions, preferably in physiologically compatible buffers such as Hank's solution, Ringer's solution, or physiological salt buffer.

Alternatively, the active ingredient may be in a powder form for constitution with a suitable vehicle, e.g., sterile, pyrogen-free water based solution, before use.

Determination of a therapeutically effective amount is well within the capability of those skilled in the art, especially in light of the detailed disclosure provided herein. For any preparation used in the methods of the invention, the therapeutically effective amount or dose can be estimated initially from in vitro assays. As shown herein in the Examples section the concentrations of LIP and hydrogen peroxide could be optimized from in vitro assays and be further adapted for an in vivo use. In addition, a dose can be formulated in tissue cultures systems or in animal models to achieve a desired concentration or titer. Such information can be used to more accurately determine useful doses in humans.

Depending on the severity of the skin pigmentation disorder (e.g., chloasma, melasma, ochronosis and lentigo) and the responsiveness of the skin, dosing can be of a single or a plurality of administrations, with course of treatment lasting from several days to several weeks or until cure is effected or diminution of the skin disorder is achieved.

The amount of a composition to be administered will, of course, be dependent on the subject being treated, the severity of the affliction, the manner of administration, the judgment of the prescribing physician, etc.

The lignin modifying enzyme included in the cosmetic composition of the present invention can be also provided at higher concentrations and be prescribed by a physician as a pharmaceutical composition to treat skin pigmentation disorders such as melasma, chloasma, ochronosis, and lentigo.

Following is a description of formulations incorporating a lignin modifying enzyme and formulated for skin or hair lightening.

Skin Lightening

To optimize and control skin lightening, the lignin modifying enzyme is preferably included in a cosmetic composition which is formulated for skin lightening purposes.

Since the skin lightening cosmetic composition of the present invention is utilized in vivo, the composition is preferably of high purity and substantially free of potentially harmful contaminants, e.g., at least National Food (NF) grade, generally at least analytical grade, and preferably at least pharmaceutical grade. To the extent that a given compound must be synthesized prior to use, such synthesis or subsequent purification shall preferably result in a product that is substantially free of any potentially contaminating toxic agents that may have been used during the synthesis or purification procedures.

Active Ingredients

A lignin modifying enzyme, such as lignin peroxidase, is included in the cosmetic composition of the present invention at a concentration selected from a range of 1-100 U/gr. According to presently known configurations the lignin modifying enzyme included in the cosmetic composition of the present invention is provided at a concentration selected from a range of 5-100 U/gr. It will be appreciated, that a preferred concentration of the lignin modifying enzyme is selected according to the specific use of the composition, thus, for general skin lightening, a preferred concentration of 5-20 U/gr is utilized, while for freckle lightening, a broader concentration range of 5-100 U/gr is utilized.

The electron acceptor (oxidizing activator), used by skin lightening cosmetic composition is preferably hydrogen peroxide provided at a concentration of at least 0.005%. Hydrogen peroxide is stable, but will decompose under neutral or alkaline conditions to form water and an active species of oxygen. The active species of oxygen are very reactive.

The cosmetic composition is preferably buffered to a pH of 4 or lower since lignin peroxidase is only active at pH below 4, preferably at pH 2.5-3.5 and hydrogen peroxide is stable at such pHs.

Any buffer capable of maintaining a pH of 4 or less may be employed. Thus, buffers employing acetic acid, tartaric acid, phosphoric acid or citric acid may be used by the skin lightening cosmetic composition.

As shown in the Examples section below, the hydrogen peroxide of the present invention is stabilized at pH 3.5 with phosphoric acid.

The oxidizing mediators used by the present invention are small aromatic molecules or more specifically methoxylated compounds that increase the oxidative potential and the stability of the lignin modifying enzyme. The preferred oxidizing mediators used by the present invention are veratryl alcohol and veratrole.

As demonstrated in the Examples section, the veratryl alcohol included in the cosmetic composition of the present invention is preferably diluted in water at a concentration of at least 0.05%.

Epidermal Penetrants

In order to enhance the percutaneous absorption of the active ingredients (e.g., LIP), one or more of a number of agents can be added to the cosmetic composition including, but not limited to, dimethylsulfoxide, dimethylacetamide, dimethylformamide, surfactants, azone, alcohol, acetone, propylene glycol and polyethylene glycol.

As illustrated in the Examples section which follows, the lignin modifying enzyme, LIP, and activator, hydrogen peroxide, are preferably mixed with epidermal penetrants such as butylene glycol and transcutol, respectively, in a manner and concentration optimized for enhancing skin penetration of the LIP. The butylene glycol used by the present invention is provided at a concentration of at least 1% and the transcutol is provided at a concentration of at least 3%.

Carriers

In addition to the pharmaceutically effective amount of an agent disclosed herein, the cosmetic composition of this aspect of the present invention also includes a dermatologically acceptable carrier.

The phrase "dermatologically acceptable carrier", refers to a carrier which is suitable for topical application onto the skin, i.e., keratinous tissue, has good aesthetic properties, is compatible with the active agents of the present invention and any other components, and is safe and non-toxic for use in mammals. An effective amount of carrier is selected from a range of about 50% to about 99.99%, preferably from about 80% to about 99.9%, more preferably from about 90% to about 98%, and most preferably from about 90% to about 95%, by weight, of the composition.

Emulsions

The carrier utilized in the compositions of the invention can be in a wide variety of forms. These include emulsion carriers, including, but not limited to, oil-in-water, water-in-oil, water-in-oil-in-water, and oil-in-water-in-silicone emulsions, a cream, an ointment, an aqueous solution, a lotion or an aerosol. As will be understood by the skilled artisan, a given component will distribute primarily into either the water or oil/silicone phase, depending on the water solubility/dispersibility of the component in the composition.

Emulsions according to the present invention generally contain a pharmaceutically effective amount of an agent disclosed herein and a lipid or oil. Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are described in, for example, U.S. Pat. No. 3,755,560, issued to Dickert, et al. Aug. 28, 1973; U.S. Pat. No. 4,421,769, issued to Dixon, et al., Dec. 20, 1983; and McCutcheon's Detergents and Emulsifiers, North American Edition, pages 317-324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, most preferably about 5 centistokes or less. The emulsion may also contain an anti-foaming agent to minimize foaming upon application to the keratinous tissue. Anti-foaming agents include high molecular weight silicones and other materials well known in the art for such use.

One type of emulsion is a water-in-silicone emulsion. Water-in-silicone emulsions contain a continuous silicone phase and a dispersed aqueous phase. Preferred water-in-silicone emulsions of the present invention comprise from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase may contain a polyorganosiloxane oil. A preferred water-in-silicone emulsion system is formulated to provide an oxidatively stable vehicle for delivery of a pharmaceutically effective amount of an agent disclosed herein. The continuous silicone phase of these preferred emulsions comprises between about 50% and about 99.9% by weight of organopolysiloxane oil and less than about 50% by weight of a non-silicone oil. In an especially preferred embodiment, the continuous silicone phase comprises at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and most preferably less than about 2%, by weight of the continuous silicone phase. These useful emulsion systems may provide more oxidative stability over extended periods of time than comparable water-in-oil emulsions containing lower concentrations of the polyorganosiloxane oil. Concentrations of non-silicone oils in the continuous silicone phase are minimized or avoided altogether so as to possibly further enhance oxidative stability of the active compound of the invention in the compositions. Water-in-silicone emulsions of this type are described in U.S. Pat. No. 5,691,380 to Mason et al., issued Nov. 25, 1997.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100 degrees Celsius. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes, which are known to those skilled in the art and commercially available.

The continuous silicone phase may contain one or more non-silicone oils. Concentrations of non-silicone oils in the continuous silicone phase are preferably minimized or avoided altogether so as to further enhance oxidative stability of the pharmaceutically effective agent in the compositions. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g., mineral oil, vegetable oils, synthetic oils, semisynthetic oils, etc.

Useful topical compositions of the present invention comprise from about 30% to about 90%, more preferably from about 50% to about 85%, and most preferably from about 70% to about 80% of a dispersed aqueous phase. The term "dispersed phase" is well-known to one skilled in the art it implies that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore. The aqueous phase can be water, or a combination of water and one or more water soluble or dispersible ingredients. Non-limiting examples of such optional ingredients include thickeners, acids, bases, salts, chelants, gums, water-soluble or dispersible alcohols and polyols, buffers, preservatives, sunscreening agents, colorings, and the like.

The topical compositions of the present invention typically comprise from about 25% to about 90%, preferably from about 40% to about 80%, more preferably from about 60% to about 80%, water in the dispersed aqueous phase by weight of the composition.

The water-in-silicone emulsions of the present invention preferably comprise an emulsifier. In a preferred embodiment, the composition contains from about 0.1% to about 10% emulsifier, more preferably from about 0.5% to about 7.5%, most preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with essential components of the composition, and provides the desired dispersion characteristics. Suitable emulsifiers include silicone emulsifiers, e.g., organically modified organopolysiloxanes, also known to those skilled in the art as silicone surfactants, non-silicon-containing emulsifiers, and mixtures thereof, known by those skilled in the art for use in topical personal care products.

Useful emulsifiers include a wide variety of silicone emulsifiers. These silicone emulsifiers are typically organically modified organopolysiloxanes, also known to those skilled in the art as silicone surfactants. Suitable emulsifiers are described, for example, in McCutcheon's, Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973.

Other preferred topical carriers include oil-in-water emulsions, having a continuous aqueous phase and a hydrophobic, water-insoluble phase ("oil phase") dispersed therein. Examples of suitable carriers comprising oil-in-water emulsions are described in U.S. Pat. No. 5,073,371 to Turner, D. J. et al., issued Dec. 17, 1991, and U.S. Pat. No. 5,073,372, to Turner, D. J. et al., issued Dec. 17, 1991. An especially preferred oil-in-water emulsion, containing a structuring agent, hydrophilic surfactant and water, is described in detail hereinafter.

A preferred oil-in-water emulsion comprises a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions of this invention comprise from about 0.5% to about 20%, more preferably from about 1% to about 10%, most preferably from about 1% to about 5%, by weight of the composition, of a structuring agent. The preferred structuring agents of the present invention are selected from the group consisting of stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

A wide variety of anionic surfactants are also useful herein. See, e.g., U.S. Pat. No. 3,929,678, to Laughlin et al., issued Dec. 30, 1975. In addition, amphoteric and zwitterionic surfactants are also useful herein.

The preferred oil-in-water emulsions comprise from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water. Suitable surfactants include any of a wide variety of known cationic, anionic, zwitterionic, and amphoteric surfactants. See, McCutcheon's. Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al. issued to Dec. 20, 1983; and U.S. Pat. No. 3,755,560. The exact surfactant chosen depends upon the pH of the composition and the other components present. Preferred are cationic surfactants, especially dialkyl quaternary ammonium compounds, examples of which are described in U.S. Pat. No. 5,151,209 to McCall et al. issued to Sep. 29, 1992; U.S. Pat. No. 5,151,210 to Steuri et al., issued to Sep. 29, 1992; U.S. Pat. No. 5,120,532; U.S. Pat. No. 4,387,090; U.S. Pat. No. 3,155,591; U.S. Pat. No. 3,929,678; U.S. Pat. No. 3,959,461; McCutcheon's, Detergents & Emulsifiers (North American edition 1979) M.C. Publishing Co.; and Schwartz, et al., Surface Active Agents, Their chemistry and Technology, New York: Interscience Publishers, 1949.

Alternatively, other useful cationic emulsifiers include amino-amides. Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

The preferred oil-in-water emulsion comprises from about 25% to about 98%, preferably from about 65% to about 95%, more preferably from about 70% to about 90% water by weight of the topical carrier.

Topical Compositions

The cosmetic composition can be formulated in any of a variety of forms utilized by the cosmetic industry for skin application including solutions, lotions, sprays, creams, ointments, salves, gels, etc., as described below.

Preferably, the cosmetic composition is formulated viscous enough to remain on the treated skin area, does not readily evaporate, and/or is not easily removed by rinsing with water, but rather is removable with the aid of soaps, cleansers and/or shampoos. Methods for preparing compositions having such properties are well known to those skilled in the art, and are described in detail in Remington's Pharmaceutical Sciences, 1990 (supra); and Pharmaceutical Dosage Forms and Drug Delivery Systems, 6th ed., Williams & Wilkins (1995).

Carriers

The topical compositions of the subject invention, including but not limited to lotions and creams, may comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients are known and may be used herein. See, e.g., Sagarin, Cosmetics, Science and Technology, 2nd Edition, Vol. 1, pp. 3243 (1972), which contains numerous examples of materials suitable as an emollient. A preferred emollient is glycerin. Glycerin is preferably used in an amount of from or about 0.001 to or about 20%, more preferably from or about 0.01 to or about 10%, most preferably from or about 0.1 to or about 5%, e.g., 3%.

Lotions and creams according to the present invention generally comprise a solution carrier system and one or more emollients. Lotions typically comprise from about 1% to about 20%, preferably from about 5% to about 10% of emollient; from about 50% to about 90%, preferably from about 60% to about 80% water; and a pharmaceutically effective amount of an agent described herein. A cream typically comprises from about 5% to about 50%, preferably from about 10% to about 20% of emollient; from about 45% to about 85%, preferably from about 50% to about 75% water; and a pharmaceutically effective amount of an agent described herein.

The topically applied cosmetic composition of the present invention may also include additional components which are added, for example, in order to enrich the cosmetic compositions with fragrance and skin nutrition factors.

Such components are selected suitable for use on human keratinous tissue without inducing toxicity, incompatibility, instability, allergic response, and the like within the scope of sound medical judgment. In addition, such optional components are useful provided that they do not unacceptably alter the benefits of the active compounds of the invention.

The CTFA Cosmetic Ingredient Handbook, Second Edition (1992) describes a wide variety of non-limiting cosmetic ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyffhizinate), skin treating agents, thickeners, and vitamins and derivatives thereof.

The cosmetic composition can be applied directly to the skin. Alternatively, it can be delivered via normal skin application by various transdermal drug delivery systems which are known in the art, such as transdermal patches that release the composition into the skin in a time released manner. Other drug delivery systems known in the arts include pressurized aerosol bottle, iontophoresis or sonophoresis. Iontophoresis is employed to increase skin permeability and facilitate transdermal delivery. U.S. Pat. Nos. 5,667,487 and 5,658,247 discloses an ionosonic apparatus suitable for the ultrasonic-iontophoretically mediated transport of therapeutic agents across the skin. Alternatively, or in addition, liposomes or micelles may also be employed as a delivery vehicle.

The active ingredients included in the cosmetic compositions of the present invention are suitable for skin lightening via the oxidation of melanin. However, the oxidation reaction can be controlled and stopped when desired by the addition of reducing reagents. These reagents can be formulated in a separate cosmetic composition and be applied on the skin when desired.

Hair Lightening

Active Ingredients

Hair lightening compositions formulated according to the teachings of the present invention include the oxidizing agent and mediator described above.

As demonstrated in the Examples section below, hair lightening can be achieved in the presence of 1.5 mM veratryl alcohol and 8.8 mM hydrogen peroxide in tartarate buffer at a pH of 3.5.

Emollients

The emollients include, but are not limited to, hydrocarbon oils and waxes, such as mineral oil, petrolatum, and the like, vegetable and animal oils and fats, such as olive oil, palm oil, castor oil, corn oil, soybean oil, and the like, and lanolin and its derivatives, such as lanolin, lanolin oil, lanolin wax, lanolin alcohols, and the like. Other emollients include esters of fatty acids having 10 to 20 carbon atoms, such as including myristic, stearic, isostearic, palmitic, and the like, such as methyl myristate, propyl myristate, butyl myristate, propyl stearate, propyl isostearate, propyl palmitate, and the like. Other emollients include fatty acids having 10 to 20 carbon atoms, including stearic, myristic, lauric, isostearic, palmitic, and the like. Emollients also include fatty alcohols having ten to twenty carbon atoms, such as cetyl, myristyl, lauryl, isostearyl, stearyl and the like.

Although some are water soluble, polyhydric alcohols and polyether derivatives are included as emollients, including glycols, glycerol, sorbitol, polyalkylene glycols and the like, such as propylene glycol, dipropylene glycol, polyethylene glycol 200-500, and the like. The water soluble examples are preferred.

Surfactants

An emulsifier/surfactant, preferably is also utilized by the hair lightening composition of the present invention.

Examples of surfactants include, but are not limited to, spolyoxyalkylene oxide condensation products of hydrophobic alkyl, alkene, or alkyl aromatic functional groups having a free reactive hydrogen available for condensation with hydrophilic alkylene oxide, polyethylene oxide, propylene oxide, butylene oxide, polyethylene oxide or polyethylene glycol Particularly effective are the condensation products of octylphenol with about 7 to about 13 moles of ethylene oxide, sold by the Rohm & Haas Company under their trademark TRITON 100® series products.

Other ingredients such as, fragrances, stabilizing agents, dyes, antimicrobal agents, antibacterial agents, anti agglomerates, ultraviolet radiation absorbers, and the like are also included in the hair lightening composition of the present invention.

Conditioners

A conditioner agent stable to acid hydrolysis, such as a silicone compound having at least one quaternary ammonium moiety along with an ethoxylated monoquat is preferably also utilized in order to stabilize and optionally thicken the hair lightening composition of the present invention.

An optional thickener also can be included to improve composition esthetics and facilitate application of the composition to the hair. Nonionic thickeners in an amount of 0% to about 3% by weight are preferred. Exemplary thickeners are methylcellulose, hydroxybutyl methylcellulose, hydroxypropylcellulose, hydroxypropyl methylcellulose, hydroxyethyl ethylcellulose and hydroxyethylcellulose, di(hydrogenated tallow) phthalic acid amide, crosslinked maleic anhydride-methyl vinyl ether copolymer, guar gum, xanthan gum and gum arabic.

The carrier of the conditioning composition is predominantly water, but organic solvents also can be included in order to facilitate manufacturing of the composition or to provide esthetic properties, such as viscosity control. Suitable solvents include the lower alcohols like ethyl alcohol and isopropyl alcohol; glycol ethers, like 2-butoxyethanol, ethylene glycol monoethyl ether, propylene glycol and diethylene glycol monoethyl ether or monomethyl ether; and mixtures thereof. Non-aqueous solvents can be present in the conditioning composition of the present invention in an amount of about 1% to about 50%, and in particular about 5% to about 25%, by weight of the total weight of the carrier in the composition.

Non-limiting conditioning agents which may be used in opaque conditioners include: stearyltrimethylammonium chloride; behenetrimethylammonium chloride; cetrimonium bromide; soytrimonium chloride; tallowtrimonium chloride; dihyrogenatedtallowedimethylammonium chloride; behentrimethylammonium methosulfate; Peg-2 Oleammonium chloride; dihyrogenatedtallowedimethylammonium bromide; dihyrogenatedtallowedimethylammonium methosulfate; palmitytrimethylammonium chloride; hydrogenated tallowtrimethylammonium chloride; hydrogenated tallowtrimethylammonium bromide; dicetyidimethylammonium chloride; distearyldimethylammonium chloride; dipalmityidimethylammonium chloride; hydrogenated tallowtrimethylammonium methosulfate; cetrimonium tosylate: eicosyltrimethylammonium chloride, and ditallowedimethylammonium chloride.

Materials that can be used to opacify compositions of the invention include fatty esters, opacifying polymers, such as styrene polymers, like OPACIFIER 653 from Morton, International, Inc.; and fatty alcohols. The following is a non-limiting list of fatty alcohols: cetyl alcohol; stearyl alcohol; cetearyl alcohol; behenyl alcohol; and arachidyl alcohol. Conditioning compositions of the invention which are not clear also can include Lexamine S-13, dicetylammonium chloride, and ceteareth-20.

Compositions of the present invention may, if desired, be presented in a dispenser device or a kit, along with appropriate instructions for use and labels indicating FDA approval for use in skin or hair lightening.

The kit for lightening a skin region or hair can include, for example, a container including a lignin modifying enzyme provided with suitable buffers, carriers, penetrants etc, and additional containers which include the oxidizing agent and mediator described above.

Lignin modifying enzymes can be also introduced into cells of the skin region by using molecular biology approaches that are known in the art.

Thus, according to yet another aspect of the present invention there is provided a method of lightening a skin region of a subject. The method according to this aspect of the present invention is effected by expressing within cells of the skin region, a lignin modifying enzyme in a manner suitable for oxidizing a pigment contained within cells of the skin region.

Such expression can be effected by transforming the cells of the skin with an expression vector which includes a lignin modifying enzyme coding sequence functionally linked to a promoter sequence.

To generate such an expression vector, a polynucleotide segment encoding a lignin modifying enzyme (e.g., the LIP H1 isoform, SEQ ID NO:1), can be ligated into a commercially available expression vector system suitable for transforming mammalian cells and for directing the expression of the lignin modifying enzyme within the transformed cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter polypeptides. Suitable mammalian expression vectors for use with the present invention include, but are not limited to, pcDNA3, pcDNA3.1(+/−), pZeoSV2(+/−), pSecTag2, pDisplay, pEF/myc/cyto, pCMV/myc/cyto, pCR3.1, which are available from Invitrogen, pCI which is available from Promega, pBK-RSV and pBK-CMV which are available from Stratagene, pTRES which is available from Clontech, and their derivatives.

A suitable expression vector for use with this aspect of the present invention is an adenovirus based vector. Adenovirus vectors have been widely used for pharmaceutical applications including cutaneous gene therapy (Ghazizadeh S, Taichman L B. (2000) Hum Gene Ther 11: 2247-51; Carter P J, Samulski R J. (2000). Int J Mol Med 6: 17-27).

The expression vector described above can be delivered into cells using a variety of delivery approaches, including, but not limited to, liposomes, epidermal patches, iontophoresis or receptor-mediated endocytosis.

In the latter approach, an antibody or ligand to a cell surface receptor that is known to undergo endocytosis, is complexed with DNA sequence encoding the lignin modifying enzyme through a covalently linked polycationic adjunct (e.g., polylysine, protamines). Such complexes retain their binding specificity to the cell surface and are taken up into the cell where they enter the endosomal compartment via normal endocytotic processes. In addition, steps must be taken to avoid degradation of the DNA within the endosome-lysosome. Cells can be treated with the lysosomatropic agent chloroquine during the transfection procedure. Alternatively, the components of viruses that enter cells by endocysis and possess an endosomal "break out" capacity can be used. Replication defective adenovirus coupled to the ligand-DNA complex gives transfection efficiencies of virtually 100% on tissue culture cells in vitro. Preliminary studies have demonstrated the potential of this method to specifically target DNA to the cell type of choice in vivo (Guy J, Drabek D, Antoniou M. (1995). Mol Biotechnol 1995 3: 237-48).

Following expression within target cells, the electron acceptor and mediator described are preferably applied to the treated region in order to facilitate lightening.

Expressing the lignin modifying enzyme within target cells is particularly advantageous since it overcomes the need for intracellular delivery of the enzyme itself, thereby potentially enhancing lightening efficiency.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

BACKGROUND

Lignin peroxidases in the P. chrysosporium fungus

There are more than 12 heme proteins displaying ligninolytic activity in the extracellular fluid of cultures of P. chrysosporium BKM-F-1767. These can be classified into two types of glycosylated heme peroxidases, lignin peroxidase (LIP) and manganese peroxidase (MNP). Isoenzymes H1, H2, H6, H7, H8 and H10 have been reported to be LIP and H3, H4, H5, and H9 have been identified as MNP (Farrell et al., 1989). The LIP isoenzymes of P. chrysosporium are encoded by a family of structurally related genes and are different in their physical characteristics, substrate specificity and stability (Farrell et al., 1989; Stewart et al., 1992). As part of the process leading to their secretion, LIP isoenzymes are proteolytically cleaved and glycosylated (Ghose, 1987; Ritch et al., 1991; Tien and Kirk, 1984). In addition, it has been reported that the LIP isoenzymes H2, H6, H8 and H10 are phosphorylated at a mannose 6-phosphate moiety, contained in asparigine-linked oligosaccharide. Analysis of aged extracellular fluid has led to the suggestion that isoenzyme H1 is probably derived from posttranslational dephosphorylation of H2 (Kuan and Tien, 1989).

The expression of the ligninolytic enzymes by P. chrysosporium is an idiophasic event triggered by nitrogen or carbon limitation and is highly dependent on culture conditions and medium composition (Dosoretz and Grethlein, 1991; Faison and Kirk, 1985; Stewart et al., 1992; van der Woude et al., 1993). The formation of LIP is particularly dependent on exposure of cultures to high oxygen tensions (Dosoretz et al., 1990; Faison and Kirk, 1985). It has been proposed that oxygen transfer into stationary cultures is restricted, and consequently a high partial pressure of oxygen in the culture headspace is needed to make sufficient oxygen available to the submerged hyphae (Leisola et al., 1983; Michel et al., 1992). LIP formation was observed in a culture that was exposed to air by immobilizing the fungus on a porous support in a non-immersed liquid culture, which improved the availability of oxygen to the fungus (Dosoretz et al., 1990; Popp et al., 1990). The concentration of $Mn^{2+}$ in the medium adversely affects the formation of LIP and MNP. While the formation of MNP is dependent on Mn, which enhances transcription of MNP, LIP formation is inhibited by Mn. Rothschild et al., (1999) showed that in both nitrogen-limited and nitrogen-excess cultures of P. chrysosporium, the high oxygen level required for LIP formation could be replaced by Mn deficiency.

Material and Experimental Methods

Growth of the fungus Phanerochaete chrysosporium for the production of lignin peroxidase—The fungus Phanerochaete chrysosporium BKMF-1767 (ATCC 24725) was maintained at 4° C. on 2% malt extract agar stock slants (Difco, Detroit, Mich., USA).

Preparation of Spore Suspension—Spores of the Fungus were Obtained by inoculating plugs from stock slants in Petri dishes containing autoclaved Potato Dextrose Agar (PDA) at a concentration of 39 g/liter. PDA plates were then incubated for up to 2 weeks at 37° C. For preparation of spore suspension, PDA plates were overlayed with 0.9% NaCl, the conidia suspension was filtered through sterile glass wool and the spore suspension collected. The spore suspension was then kept frozen at −80° C.

Inoculum preparation—Spores were inoculated into a sterilized inoculum medium (see formulation hereinbelow) at a final concentration of $7.5 \times 10^5$ spores/ml. Ninety ml of the mixture were added to each fermentation batch (Tien and Kirk, 1988. Meth. Enzymol. 161: 238-490; Dosoretz et al., 1990, Appl. Microbiol. Biotechnol. 34: 131-7), and the batches were then sealed with cotton stoppers. The cultures were grown statically for 48 h at 37° C. as shallow cultures. For inoculation of cultures the fermentation batch contents were blended for 2 min with a mixer (Waring, England).

Growth of the fungus in stirred tank reactor (STR) fermentor—Prior to fungus growth, polyurethane foam was settled around the cooling tubes of the fermentor and the whole STR fermentor was sterilized. Ten liters of a fermentor medium (see formulation hereinbelow) were then poured into the STR fermentor and 900 ml of blended inoculum (the content of 10 fermentation batches) were added. The fermentor was connected to a cooling system to maintain a temperature of 37° C. and was stirred at 100 rpm. Sterilized air was introduced into the fermentor at 2 ml/min. The flow was changed to 4 ml/min after 2 days of growth. The growth was continued for 3-5 days.

Inoculum medium was prepared by mixing the following solutions and was sterilized with a 0.45 μm filter membrane (Micron Separations Inc (MSI), Westborough, MA, USA). For preparation of 1 liter of liquid medium, the following components were combined: 100 ml Basic Medium for P. chrysosporium growth×10 (see formulation below) 10 ml $CaCl_2$ stock solution (13.2 g/l) (Sigma-Aldrich Corp., St Louis, Mo., USA). Final concentration 0.132 g/L 12 ml glycerol stock solution (50 g/100-ml) (Frutarom, Israel). Final concentration 6 g/L.

Doubled distilled water is added to 1 liter.

Fermentor medium was prepared in the following way and was sterilized with a 0.45 μm filter membrane (MSI, Westborough, Mass., USA). For preparation of 10 liters of liquid medium, the following components were combined:

100 ml $CaCl_2$ stock solution (13.2 g/l) (Sigma, USA). Final concentration 0.0132 g/l 120 ml glycerol stock solution (50 g/100-ml) (Frutarom, Israel). Final concentration 6 g/l.

50 ml of Tween-80 stock solution (10.8 ml/100 ml) (Sigma, USA). Final concentration 0.54 ml/l 1000 ml of Basic Medium for P. chrysosporium growth×10 (see formulation below) 3.36 g of veratryl alcohol (Sigma, USA). Final concentration 2 mM.

7.740 liters of double distilled water (DDW) to a final volume of 10 liters.

Basic Medium for P. chrysosporium growth×10—Basic medium for P. chrysosporium growth×10 was prepared as follows: 7.07 gr Nitrilotriacetic acid (trisodium salt) were dissolved in 4 liters of DDW. The following reagents were then added: 100 gr $KH_2PO_4$ anhydrous, 72.7 gr $MgSO_4.7H_2O$ (or 67.39 gr $MgSO_4.6H_2O$), 3.5 gr NaCl, 0.35 gr $FeSO_4.7H_2O$, 0.63 gr $CoCl_2.6H_2O$, 0.35 gr $ZnSO_4.7H_2O$, 0.055 gr $CuSO_4.5H_2O$, 0.035 gr $AlK(SO_4)_2.12H_2O$, 0.035 gr $H_3BO_3$, 0.035 gr $Na_2MoO_4.2H_2O$, 500 ml 2M acetate buffer pH 4.5, 10 gr ammonium tartrate and 50 mg Thiamine. All supplied by Sigma-Aldrich Corp., St Louis, Mo., USA. The pH was of the medium was adjusted to 4.4-4.45 with NaOH and DDW was added to a final volume of 5 liters. Medium was stored at 4° C.

Isolation and purification of LIP from the extracellular medium of Phanerochaete chrysosporium—The extracellular medium was vacuum filtered through a glass fiber. The filtrate was then sterilized with a 0.45 μM filter membrane (MSI, Westborough, Mass., USA) and the fluid was concentrated by a hollow fiber membrane using a peristaltic pump (MASTERFLEX, Vernon Hills, Ill., USA). The concentrated extracellular fluid was then re-concentrated 25-fold by ultrafiltration using a 10-kDa-cutoff type PM-10 membrane (Amicon, Danvers, Mass.), and purified with a Mono Q column (HR5/5, Pharmacia, Piscataway, N.J.) by HPLC-anion exchange chromatography using two gradients of 0.01-1.00 M sodium acetate. The first gradient was at pH 6.0 and the second gradient was at pH 4.7, which is equivalent to the isoelectric point (pI) value of LIP isoenzyme H1. Protein peaks were collected and their activity was assayed using purified LIP isoenzyme H1 from a previous batch as standard. Absorbance of the LIP H1 fraction was measured at: 280 nm, and 409 nm (Hewlett Packard, Waldbronn, Germany). The degree of purity (RZ), calculated from the ratio between the absorbance at 409 nm ($A_{409}$) and absorbance at 280 nm ($A_{280}$) of purified LIP isoenzyme H1 was greater than 4.0. LIP concentration was determined at 409 nm using an extinction coefficient of $169 M^{-1} cm^{-1}$.

Assay of LIP activity—LIP activity was measured by the change in absorbance at 310 during the oxidation of veratryl alcohol to veratryl aldehyde as described by Tien and Kirk (1988). The assay reagent is composed of 4 mM veratryl alcohol and 0.88 mM $H_2O_2$ in 100 mM Tartarate buffer at pH 2.5. For the assay, 0.5 ml of *P. chrysosporium* extracellular medium was mixed with 0.5 ml of the reagent and the increase in absorbance at 310 nm was recorded for 40 sec. One unit of LIP is defined as 1 µmole of veratryl alcohol oxidized to veratryl aldehyde per minute.

Determination of melanin oxidation by LIP—Synthetic Melanin (Sigma, Cat # M8631, St Louis Mo., USA) was prepared at various concentrations in 50 mM Tris buffer at pH 8.00. The oxidation of melanin by LIP was carried out in Tartarate buffer at pH 3.5 containing veratryl alcohol, and the enzymatic reaction was initiated by the addition of hydrogen peroxide. Degree of melanin oxidation was determined by measuring the decrease in absorbance at 460 nm.

Cream preparation—The LIP cream in the preferred embodiments is composed of two kinds of creams: the enzyme cream and the activator cream. Each cream was prepared from two phases, i.e., the water phase and the oil phase.
Enzyme Cream
Water phase for the enzyme cream:
0.35% (w/w) DMDM hydantoin (Sharon Lab, Israel);
2% (w/w) glycerine (Cognis, Germany);
0.1% (w/w) veratryl alcohol (3-dimethoxybenzyl alcohol, Sigma, USA);
81.65% (w/w) DDW (RO Water, Israel);
0.2% (w/w) Rhodicare D (xanthan gum, Rhodia, France);
4% (w/w) transcutol (PEG-400, ethoxydiglycol, Gattefosse, France);
Oil phase for the enzyme cream:
5% light mineral oil;
2.5% (w/w) dragorin 100 SEP (GMS & PEG-100 stearate, Dragoco, Germany);
3% (w/w) cetyl alcohol (Cognis, Germany);
0.2% (w/w) Potassium sorbate (Chisso Corp., Japan);
1% (w/w) brij 721 (Uniqema, Italy).

Preparation of the enzyme cream: the water and oil phases of the enzyme cream were heated to 80° C. and then mixed. The mixture was homogenized for 10 min and cooled to 55° C. Afterwards the pH was adjusted to 3.5 with lactic acid. When the mixture cooled to 40° C., lignin peroxidase was added (20-50 Units/gr). The enzyme mixture was homogenized for 1 min.
Activator Cream
Water phase for the activator cream:
82.888 (w/w) DDW (RO Water, Israel);
0.1% (w/w) EDTA disodium (Merck, Germany);
4% (w/w) transcutol (PEG-400, ethoxydiglycol, Gattefosse, France);
0.1% (w/w) Potassium sorbate (Chisso Corp., Japan);
Oil phase for the activator cream:
3.5% (w/w) brij 72 (Steareth-2, Uniqema, Italy);
2.5% (w/w) brij 721 (Steareth-20, Uniqema, Italy);
5% (w/w) mineral oil;
1.3% (w/w) cetyl alcohol (Cognis, Germany);
0.5% (w/w) silicon 350 (Dimethicon, Dow Corning, USA);
0.1% (w/w) Potassium sorbate (Chisso Corp., Japan).

Preparation of the activator cream—The water and oil phases of the activator cream were heated to 80° C. and mixed. The mixture was homogenized for 10 min, cooled to 45° C. and adjusted to pH 3.5 with phosphoric acid.

When the mixture had cooled to 40° C. hydrogen peroxide (Riedel-de Haen, Germany) was added (0.012% (w/w)) with gentle stirring, correct pH was verified and the activator mixture was homogenized for 1 min.

Determination of skin lightening effect in vivo—In order to quantitate the effect of LIP on skin lightening the skin color of the treated hand was tested using three wavelength of the Minolta chromameter (CR-200 Japan): Minolta L measures darkness and brightness, Minolta A measures red tones and Minolta B measures yellow tones. The increase in Minolta L values reflects the degree of skin brightness, i.e., higher values correspond to brighter skin.

Experimental Results

Example 1

Purification of LIP from *P. chrysosporium*

Figure 1:
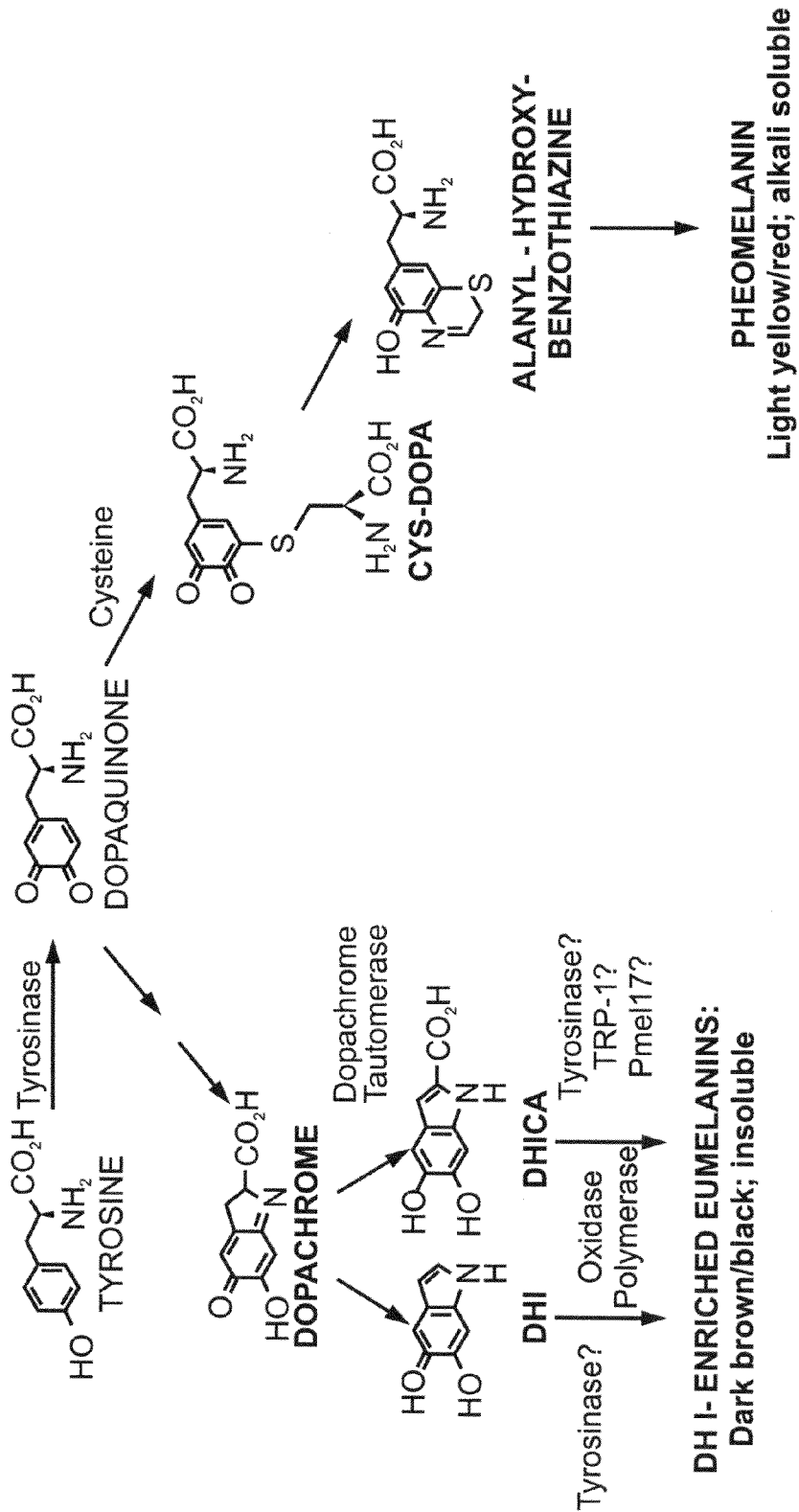
Figure 2:
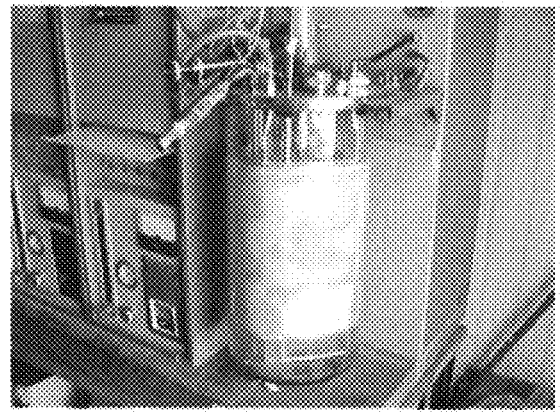

Preparation of highly purified LIP H1 from *P. chrysosporium*—In order to purify LIP isoenzyme H1 from *P. chrysosporium* the fungus was grown in an STR fermentor (FIG. 2) as described in detail in the Methods section hereinabove. Initial LIP activity was detected after 48 hr of growth and significant increases in activity were detected when growth was maintained up to 120 hr (FIG. 3). For the purification of LIP isoenzyme H1 the extracellular fluid of the fungus was collected at peak LIP activity (120 hr). The LIP isoenzyme H1 protein was then purified and its concentration was determined as described under Methods. Thus, using the above-mentioned apparatus and conditions, LIP can be reliably produced and its H1 isoenzyme can be purified by HPLC.

Example 2

Optimization of Melanin in an Aqueous Phase Oxidation Using Purified LIP

In order to optimize the conditions needed for melanin oxidation by LIP, optimal concentration of each of the critical components of the oxidation reaction was determined independently.

LIP oxidization of melanin in an aqueous phase, is a function of hydrogen peroxide concentration—Oxidation of melanin by LIP in an aqueous phase was first tested for correlation to hydrogen peroxide concentrations. A constant concentration of melanin (70.5 µg/ml) was oxidized by 0.48 µM of purified LIP H1 in the presence of 1.5 mM veratryl alcohol and with increasing concentrations of hydrogen peroxide. Degree of oxidation was determined by measuring melanin's absorbance at 460 nm, before the addition of hydrogen peroxide and 160 sec after that, and was calculated in percentages. Generally, the oxidation of melanin increased with increasing concentrations of hydrogen peroxide up to a plateau that was obtained at 700-900 µM of hydrogen peroxide (FIG. 4). The effect of peroxide concentration on melanin oxidation is further demonstrated by comparison of reaction mixtures in FIG. 5, where the reaction mixture is significantly lightened with increasing hydrogen peroxide concentrations. Thus, these results demonstrate that LIP oxidation of melanin in an aqueous phase is clearly dependent on hydrogen peroxide concentrations, optimal concentrations of hydrogen peroxide for the oxidation of melanin being in the range of 600 µM to 700 µM.

LIP oxidation of melanin is a function of melanin's initial concentration in an aqueous phase—In order to determine the optimal melanin concentration required for oxidation of melanin in an aqueous phase by LIP the oxidation reaction was further tested with increasing melanin concentrations. Oxidation of melanin took place by 0.48 µM of purified LIP H1 in the presence of 1.5 mM veratryl alcohol and 600 µM hydrogen peroxide. At initial melanin concentrations between 15 to 45 µg/ml, melanin oxidation by LIP was dependent on the initial concentrations of melanin. Maximal oxidation of melanin (60%) was reached at melanin initial concentrations between 45 to 85 µg/ml (FIG. 6). Thus, melanin oxidation by LIP is clearly independent of initial melanin concentrations, beyond 45 µg/ml.

Melanin oxidation of LIP is partially dependent on LIP concentration in an aqueous phase—To further optimize the conditions for melanin oxidation, the effect of LIP concentration on melanin oxidation was tested with optimal concentrations of melanin (70 µg/ml), hydrogen peroxide (700 µM) and veratryl alcohol (1.5 mM). Melanin oxidation was drastically increased from 10 to 60% when LIP concentration was increased from 0.25 µM to 0.40 µM. However, beyond LIP concentration of 0.50 µM no change in melanin oxidation was observed (FIG. 7). Thus, the optimal range of LIP concentrations for melanin oxidation in vitro is 0.40-0.50 µM.

Example 3

Oxidation of Melanin Using LIP in a Cream Formulation

To further substantiate the ability of LIP isoenzyme H1 to oxidize melanin and as an intermediate step towards skin lightening in vivo, the LIP activity was tested in a cream formulation on melanin solubilized in an aqueous phase.

Melanin in an aqueous phase is oxidized by LIP in a cream formulation—Two types of cream were prepared: the enzyme cream comprising the LIP isoenzyme H1 fraction (25 units/gr cream) and veratryl alcohol (6 mmole/Kg cream), and the activator cream comprising hydrogen peroxide (3.52 mmole/Kg cream). For determination of LIP activity in a cream formulation the enzyme cream (0.3 gr) was first mixed with melanin (140 µg/ml) and a grayish black color was observed (FIG. 8a). When the activator cream (0.3 gr) was added to the enzyme cream already containing melanin, the color was immediately changed to beige (FIG. 8b). These results demonstrate that LIP in a cream formulation is highly efficient in melanin decolorization and can further be tested on human skin.

Example 4

In Vivo Skin and Hair Lightening by Purified LIP H1 in a Cream Formulation

To test the ability of LIP to lighten skin and hair in vivo the enzyme in a cream and aqueous formulations was added to skin and hair, respectively.

LIP in a cream formulation lightens skin in vivo—To test the ability of LIP in a cream formulation to lighten skin in vivo, the enzyme cream was applied and absorbed by the skin and then the activator cream was applied four times in 5 min intervals. When repeated twice a day for one week a significant lightening of the treated skin areas was observed (FIG. 9). When skin color of two areas of the treated hand was quantitated using a Minolta chromameter, a clear skin-lightening effect of two week's application of LIP cream was observed (Table 1, % change). Thus, these results demonstrate that LIP, prepared in an easy to apply cream formulation can simply and efficiently lighten skin in vivo, and that LIP prepared as detailed herein may be further adapted for other in vivo lightening applications.

TABLE 1

QUANTIFICATION OF SKIN LIGHTENING IN VIVO

| | | Minolta L (bright) | Minolta A (red) | Minolta B (yellow) |
|---|---|---|---|---|
| Area I | Baseline | 44.8 | 10.5 | 16.34 |
| Area I | 2 weeks | 48.8 | 10.6 | 17.93 |
| Area I | % change | 8.9 | — | 9.7 |
| Area II | Baseline | 49.91 | 10.38 | 19.28 |
| Area II | 2 weeks | 53.8 | 9.39 | 20.63 |
| Area II | % change | 7.79 | — | 7.0 |

Table 1 illustrates three sets of readings in absolute numbers taken from the Minolta chromameter of two areas in the treated hand. Area I corresponds to the circled area in FIG. 9, area II corresponds to data not shown.

LIP in an aqueous formulation lightens hair in vivo—Lightening of pigmentation is often required in melanin-rich tissues other than skin. To further test its in vivo lightening effects, LIP was applied on human hair. Before LIP application, the hair was first immersed for 1 hr in 50 mM carbonate buffer at pH 11.5 and then transferred to another tube containing LIP (25 U/20 µl in water). The hair was incubated with LIP for 10 seconds and then transferred into tartarate buffer at pH 3.5 in the presence of veratryl alcohol (1.5 mM) and hydrogen peroxide (8.8 mM). A significant lightening effect was observed within 1 hr in the presence of LIP (FIG. 10, right tube) as compared with the hair treated in the same solution but without LIP (FIG. 10, left tube). Thus, these results demonstrate that in the presence of very low concentrations of hydrogen peroxide LIP in an aqueous formulation can efficiently lighten hair in vivo.

Example 5

Scaling up of LIP Preparation Process

In order to produce large quantities of lignin peroxidase (LIP) useful for commercial purposes LIP was purified from the *P. chrysosporium* fungus using a scaled up protocol.

High activity of LIP obtained using a scaled-up fermentation protocol—Fermentation was performed in a 100 L fermentor using 90 L fermentation medium as described in the Methods section hereinabove. Fermentation conditions included agitation of 160 rpm and air flow of 0.2 vvm. Inoculation was performed in the same way as in the 10 L fermentor which is described in the Methods section hereinabove. Following 7 days of growth the measured LIP activity was 1600 units/liter.

These results demonstrate that large quantities and high catalytic activities of LIP can be produced from the *P. chrysosporium* fungus using large fermentors and the scaled up protocol of the present invention.

Example 6

Dermatological Testes for the LIP Cream: Hypoallergenic, Sensitive Skin, and Sensitizing and Challenging Tests on Normal Skin To characterize the dermatological properties of the LIP cream and as a prerequisite for use as a cosmetic product the LIP cream was subjected to several dermatological tests: an hypoallergenic test, a sensitizing and challenging test on normal skin, and a sensitizing and challenging test on sensitive skin.

Methods

Study subjects for dermatological tests on normal skin: The study included 50 volunteers, 9 males and 41 females, in a range of ages from 18 to 64 years. The volunteers were in a good general health and free of any visible skin disease or anomaly in the area to be patched. Each study subject was required to read, understand and sign an informed consent statement. The exclusion criteria were the following: pregnant or nursing women, subjects suffering from serious or progressive diseases and/or pathology on the treated zone, subjects using a treatment (e.g., retinoids, steroids) and/or modifiers of the cutaneous hydration, subjects with unstable weight or excessive use of alcohol or tobacco.

A summary of the characteristics of the study subjects is presented in Table 2 hereinbelow.

TABLE 2

THE CHARACTERISTICS OF THE STUDY SUBJECTS

| Sex | Average age (years) | Medical history likely to influence the study |
|---|---|---|
| F | 40.36 | None |
| M | 34.33 | None |

Study subjects for the dermatological test on sensitive skin—A total of 50 subjects, 6 males and 44 females completed the test: 22 subjects were in the range of 18 to 35, 11 subjects in the range of 36 to 45, and 17 subjects in the range of 46 to 65.

Associated treatment during the study—No water was applied to the test site during application of the patch; no systemic or topical treatment likely to modify the skin was permissible; no use of dermopharmaceutical or cosmetic products, including cleansing products, was permissible on the zones being evaluated.

Patch preparation—For the hypoallergenic test, 2 mg of the LIP cream of the present invention was placed in a Curatest® F adhesive strip (Lohmann & Rauscher International GmbH & Co. KG, Rengsdort). For the dermatological tests and sensitive skin tests each patch included 0.07-0.1 grams of the LIP cream in the Curatest® F adhesive strip.

The Draize Repeated Insult patch test was carried out essentially as described in "Appraisal of the Safety of Chemicals in Foods, Drugs and Cosmetics" by J. H. Draize (published by the Association of Food and Drug Officials of the United States).

Induction phase—The patch was applied on designated contact sites and remained in place for 24 hours. At the end of this period the patch was removed and the site was examined for any dermal response. The study subjects rested for 24 hours, after which the skin site was examined again. A patch was then applied to the same site as previously used. The second application was identical to the first and remained in place 24 hours. This procedure was repeated nine times. The study subjects examined the site for any dermal response and reported their observations prior to the next application. The same site was used throughout the study. Each application was put on and removed by the staff of the Institute of Skin Research (Tel Aviv, Israel). A quality control person monitored the adherence to study protocol.

Challenge phase—Following the 9th application, a rest period of 2 weeks elapsed after which a challenge application was applied in the same manner and to the same site used during the induction phase. The challenge application was removed after 24 hours and the site was examined and graded for signs of irritation or sensitization. A follow-up examination was conducted at 48 hours after the challenge application (24 hours after patch removal), as well as at 48 and 72 hours after removal.

Grading scale—The results of the induction and challenge tests were graded using the following scale: "0"=No visible reaction; "?"=doubtful reaction, i.e., faint, minimal erythema, no infiltration; "1"=weak positive reaction, i.e., erythema, infiltration, no discrete papules; "2"=strong positive reaction, i.e., erythema, infiltration, papules, discrete vesicles; "3"=extra positive reaction, i.e., intense erythema, infiltration, coalescing vesicles/bullous reaction; "IR"=irritation reaction, i.e., discrete erythema without infiltration/patchy follicular erythema/hemorrhagic and follicular pustules; "NT"=not tested.

Dermatological Tests Results

Hypoallergenic test—In this test the reaction to the application of a patch containing the LIP cream was recorded following 20 minutes, 24 hours and 48 hours of patch removal. As is shown in Table 3 hereinbelow, in all 50 study subjects there was no visible skin reaction to the LIP cream.

TABLE 3

Results of hypoallergenic test

| No | Subject | Sex | Age | 20 minutes | 24 hours | 48 hours |
|---|---|---|---|---|---|---|
| 1 | D.P. | M | 37 | 0 | 0 | 0 |
| 2 | G.B. | F | 62 | 0 | 0 | 0 |
| 3 | Z.A. | F | 58 | 0 | 0 | 0 |
| 4 | S.E. | F | 64 | 0 | 0 | 0 |
| 5 | E.R | F | 61 | 0 | 0 | 0 |
| 6 | G.C. | F | 35 | 0 | 0 | 0 |
| 7 | S.S. | F | 26 | 0 | 0 | 0 |
| 8 | D.P. | F | 65 | 0 | 0 | 0 |
| 9 | E.T. | F | 46 | 0 | 0 | 0 |
| 10 | I.M. | F | 58 | 0 | 0 | 0 |
| 11 | M.I. | F | 40 | 0 | 0 | 0 |
| 12 | G.O. | F | 30 | 0 | 0 | 0 |
| 13 | M.L. | F | 49 | 0 | 0 | 0 |
| 14 | S.A. | M | 22 | 0 | 0 | 0 |
| 15 | C.B. | F | 38 | 0 | 0 | 0 |
| 16 | B.A. | F | 34 | 0 | 0 | 0 |
| 17 | S.I. | F | 45 | 0 | 0 | 0 |
| 18 | K.S. | F | 35 | 0 | 0 | 0 |
| 19 | S.S. | F | 28 | 0 | 0 | 0 |
| 20 | F.H. | F | 26 | 0 | 0 | 0 |
| 21 | R.S. | F | 44 | 0 | 0 | 0 |
| 22 | A.A. | F | 25 | 0 | 0 | 0 |
| 23 | S.T. | M | 21 | 0 | 0 | 0 |
| 24 | F.A. | M | 38 | 0 | 0 | 0 |
| 25 | S.S. | F | 42 | 0 | 0 | 0 |
| 26 | S.R. | M | 49 | 0 | 0 | 0 |
| 27 | S.I. | M | 19 | 0 | 0 | 0 |
| 28 | C.T. | F | 32 | 0 | 0 | 0 |
| 29 | C.J. | M | 35 | 0 | 0 | 0 |
| 30 | H.P. | F | 30 | 0 | 0 | 0 |
| 31 | F.S. | F | 36 | 0 | 0 | 0 |
| 32 | P.A. | F | 45 | 0 | 0 | 0 |

TABLE 3-continued

Results of hypoallergenic test

| No | Subject | Sex | Age | 20 minutes | 24 hours | 48 hours |
|----|---------|-----|-----|------------|----------|----------|
| 33 | P.N. | M | 51 | 0 | 0 | 0 |
| 34 | M.R. | F | 30 | 0 | 0 | 0 |
| 35 | S.L. | F | 31 | 0 | 0 | 0 |
| 36 | T.I. | F | 23 | 0 | 0 | 0 |
| 37 | V.I. | F | 30 | 0 | 0 | 0 |
| 38 | L.A. | F | 45 | 0 | 0 | 0 |
| 39 | T.R. | F | 43 | 0 | 0 | 0 |
| 40 | C.D. | F | 38 | 0 | 0 | 0 |
| 41 | S.S. | F | 36 | 0 | 0 | 0 |
| 42 | L.B. | F | 36 | 0 | 0 | 0 |
| 43 | M.L. | F | 31 | 0 | 0 | 0 |
| 44 | A.T. | M | 37 | 0 | 0 | 0 |
| 45 | G.K. | F | 42 | 0 | 0 | 0 |
| 46 | B.P. | F | 51 | 0 | 0 | 0 |
| 47 | L.T. | F | 56 | 0 | 0 | 0 |
| 48 | I.V. | F | 35 | 0 | 0 | 0 |
| 49 | P.O. | F | 43 | 0 | 0 | 0 |
| 50 | C.P. | F | 31 | 0 | 0 | 0 |

Table 3: The results of an hypoallergenic test as was graded 20 minutes, 24 hours or 48 hours following the removal of the application.

Sensitizing and challenging normal skin with the LIP cream resulted in absence of any skin reaction—The LIP cream was inserted into the patches and the Draize Repeated Insult patch test was carried out on 50 healthy volunteers. Following each patch application, the skin reaction was recorded using the grading scale described in the Methods section hereinabove. As is shown in Table 4 hereinbelow, in all 50 volunteers there was no visible skin reaction during all 9 cream applications of the induction phase as well as following the last application of the challenging phase.

TABLE 4

The results of the induction and challenge tests of the LIP cream

| | | | | Results according to the grading scale | | | | | | | | | |
|---|---|---|---|---|---|---|---|---|---|---|---|---|---|
| No. | Subject | Sex | Age | 1 | 2 | 3 | 4 | 5 | 6 | 7 | 8 | 9 | 10 |
| 1. | D.P. | M | 37 | 0 | 0 | 0 | 0 | 0 | 0 | 0 | 0 | 0 | 0 |
| 2. | G.B. | F | 62 | 0 | 0 | 0 | 0 | 0 | 0 | 0 | 0 | 0 | 0 |
| 3. | Z.A. | F | 58 | 0 | 0 | 0 | 0 | 0 | 0 | 0 | 0 | 0 | 0 |
| 4. | S.E. | F | 64 | 0 | 0 | 0 | 0 | 0 | 0 | 0 | 0 | 0 | 0 |
| 5. | E.R | F | 61 | 0 | 0 | 0 | 0 | 0 | 0 | 0 | 0 | 0 | 0 |
| 6. | G.C. | F | 35 | 0 | 0 | 0 | 0 | 0 | 0 | 0 | 0 | 0 | 0 |
| 7. | S.S. | F | 26 | 0 | 0 | 0 | 0 | 0 | 0 | 0 | 0 | 0 | 0 |
| 8. | D.P. | F | 65 | 0 | 0 | 0 | 0 | 0 | 0 | 0 | 0 | 0 | 0 |
| 9. | E.T. | F | 46 | 0 | 0 | 0 | 0 | 0 | 0 | 0 | 0 | 0 | 0 |
| 10. | I.M. | F | 58 | 0 | 0 | 0 | 0 | 0 | 0 | 0 | 0 | 0 | 0 |
| 11. | M.I. | F | 40 | 0 | 0 | 0 | 0 | 0 | 0 | 0 | 0 | 0 | 0 |
| 12. | G.O. | F | 30 | 0 | 0 | 0 | 0 | 0 | 0 | 0 | 0 | 0 | 0 |
| 13. | M.L. | F | 49 | 0 | 0 | 0 | 0 | 0 | 0 | 0 | 0 | 0 | 0 |
| 14. | S.A. | M | 22 | 0 | 0 | 0 | 0 | 0 | 0 | 0 | 0 | 0 | 0 |
| 15. | C.B. | F | 38 | 0 | 0 | 0 | 0 | 0 | 0 | 0 | 0 | 0 | 0 |
| 16. | B.A. | F | 34 | 0 | 0 | 0 | 0 | 0 | 0 | 0 | 0 | 0 | 0 |
| 17. | S.I. | F | 45 | 0 | 0 | 0 | 0 | 0 | 0 | 0 | 0 | 0 | 0 |
| 18. | K.S. | F | 35 | 0 | 0 | 0 | 0 | 0 | 0 | 0 | 0 | 0 | 0 |
| 19. | S.S. | F | 28 | 0 | 0 | 0 | 0 | 0 | 0 | 0 | 0 | 0 | 0 |
| 20. | F.H. | F | 26 | 0 | 0 | 0 | 0 | 0 | 0 | 0 | 0 | 0 | 0 |
| 21. | R.S. | F | 44 | 0 | 0 | 0 | 0 | 0 | 0 | 0 | 0 | 0 | 0 |
| 22. | A.A. | F | 25 | 0 | 0 | 0 | 0 | 0 | 0 | 0 | 0 | 0 | 0 |
| 23. | S.T. | M | 21 | 0 | 0 | 0 | 0 | 0 | 0 | 0 | 0 | 0 | 0 |
| 24. | F.A. | M | 38 | 0 | 0 | 0 | 0 | 0 | 0 | 0 | 0 | 0 | 0 |
| 25. | S.S. | F | 42 | 0 | 0 | 0 | 0 | 0 | 0 | 0 | 0 | 0 | 0 |
| 26. | S.R. | M | 49 | 0 | 0 | 0 | 0 | 0 | 0 | 0 | 0 | 0 | 0 |
| 27. | S.I. | M | 19 | 0 | 0 | 0 | 0 | 0 | 0 | 0 | 0 | 0 | 0 |
| 28. | C.T. | F | 32 | 0 | 0 | 0 | 0 | 0 | 0 | 0 | 0 | 0 | 0 |
| 29. | C.J. | M | 35 | 0 | 0 | 0 | 0 | 0 | 0 | 0 | 0 | 0 | 0 |
| 30. | H.P. | F | 30 | 0 | 0 | 0 | 0 | 0 | 0 | 0 | 0 | 0 | 0 |
| 31. | F.S. | F | 36 | 0 | 0 | 0 | 0 | 0 | 0 | 0 | 0 | 0 | 0 |
| 32. | P.A. | F | 45 | 0 | 0 | 0 | 0 | 0 | 0 | 0 | 0 | 0 | 0 |
| 33. | P.N. | M | 51 | 0 | 0 | 0 | 0 | 0 | 0 | 0 | 0 | 0 | 0 |
| 34. | M.R. | F | 30 | 0 | 0 | 0 | 0 | 0 | 0 | 0 | 0 | 0 | 0 |
| 35. | S.L. | F | 31 | 0 | 0 | 0 | 0 | 0 | 0 | 0 | 0 | 0 | 0 |
| 36. | T.I. | F | 23 | 0 | 0 | 0 | 0 | 0 | 0 | 0 | 0 | 0 | 0 |
| 37. | V.I. | F | 30 | 0 | 0 | 0 | 0 | 0 | 0 | 0 | 0 | 0 | 0 |
| 38. | L.A. | F | 45 | 0 | 0 | 0 | 0 | 0 | 0 | 0 | 0 | 0 | 0 |
| 39. | T.R. | F | 43 | 0 | 0 | 0 | 0 | 0 | 0 | 0 | 0 | 0 | 0 |
| 40. | C.D. | F | 38 | 0 | 0 | 0 | 0 | 0 | 0 | 0 | 0 | 0 | 0 |
| 41. | S.S. | F | 36 | 0 | 0 | 0 | 0 | 0 | 0 | 0 | 0 | 0 | 0 |
| 42. | L.B. | F | 36 | 0 | 0 | 0 | 0 | 0 | 0 | 0 | 0 | 0 | 0 |
| 43. | M.L. | F | 31 | 0 | 0 | 0 | 0 | 0 | 0 | 0 | 0 | 0 | 0 |
| 44. | A.T. | M | 37 | 0 | 0 | 0 | 0 | 0 | 0 | 0 | 0 | 0 | 0 |
| 45. | G.K. | F | 42 | 0 | 0 | 0 | 0 | 0 | 0 | 0 | 0 | 0 | 0 |
| 46. | B.P. | F | 51 | 0 | 0 | 0 | 0 | 0 | 0 | 0 | 0 | 0 | 0 |
| 47. | L.T. | F | 56 | 0 | 0 | 0 | 0 | 0 | 0 | 0 | 0 | 0 | 0 |
| 48. | I.V. | F | 35 | 0 | 0 | 0 | 0 | 0 | 0 | 0 | 0 | 0 | 0 |

TABLE 4-continued

The results of the induction and challenge tests of the LIP cream

| | | | | Results according to the grading scale | | | | | | | | | |
|---|---|---|---|---|---|---|---|---|---|---|---|---|---|
| No. | Subject | Sex | Age | 1 | 2 | 3 | 4 | 5 | 6 | 7 | 8 | 9 | 10 |
| 49. | P.O. | F | 43 | 0 | 0 | 0 | 0 | 0 | 0 | 0 | 0 | 0 | 0 |
| 50. | C.P. | F | 31 | 0 | 0 | 0 | 0 | 0 | 0 | 0 | 0 | 0 | 0 |

Table 4: Grading scores following each patch application in the induction phase (scoring results Nos. 1-9) and the challenge phase (scoring results No. 10).
M = male;
F = female.

Dermatological test on sensitive skin—To further characterize the sensitizing properties of the LIP cream an irritation patch test was carried out on 50 healthy volunteers with sensitive skin. At the pretest, 11 subjects were found to have various degrees of stinging: 2 with severe sensitive skin, 8 with moderately sensitive skin and 1 with slightly sensitive skin. The irritating patch including the LIP cream was placed on the back of the volunteers for 48 hours. The tested area was inspected following 1 hr, 24 hrs and 48 hours and it was found that there was no skin reaction in any of the 50 volunteers.

These results rule out hypoallergenic and irritating reactions to the LIP cream in normal and sensitive skin. Moreover, the results of the Repeated Insult patch test further suggest the use of the LIP cream as a safe cosmetic composition.

Example 7

Lip Cream is Highly Efficient in Whitening Skin Pigmentation

The effect of the LIP cream in skin whitening was compared to prior art creams in a double blind study.
Study Design
Study subjects—The study included 12 healthy males and females at ages 18-65 of Asian origin which were free of disease, with no history of skin diseases or atopic diseases (asthma, hay fever, allergic rhinitis) and no known sensitivity to any of the substances being tested and any of the components of the cosmetic preparation. The study excluded candidates who were undergoing treatment with anti-inflammatory drugs, antihistamines, or corticosteroids for systemic or local treatment, unless the treatment was interrupted two weeks in the case of systemic treatment and three days in the case of local treatment prior to enrolling in the study. Also excluded from study candidates with cancer, kidney disease or liver disease at any stage of diagnosis or treatment, as well as pregnant and breast-feeding women.

Study protocol—The study included two types of creams which were applied in a double blind fashion each on one upper forearm: the whitening cream of the present invention which includes LIP as the active ingredient, and a marketed product, 2% Hydroquinone (Esomed Medibrands, Israel). The creams were applied twice a day (i.e., morning and evening). The lower parts of the forearms remained untreated. Study subjects were examined by the staff of the Institute of Skin Research (Tel Aviv, Israel), at the beginning of the study (week 0), and following one, two and three weeks of cream application. At each examination skin pigmentation and side effects were recorded.

Evaluation of skin pigmentation—Skin pigmentation was evaluated using a Derma Spectrometer (Cortex Technology, Denmark), color photographs which were taken using the same distance and light exposure and visual inspection made by Prof. Brenner (Head of the Dermatological Department, Souraski Medical Center, Tel Aviv, Israel) and her team.
Study Results The LIP cream reduced skin pigmentation after 3 weeks of application—To evaluate the effect of the LIP cream in skin whitening the LIP cream was applied twice a day on the upper part of the right arm of 12 healthy volunteers. As is shown in FIGS. 11a-b and 13a-b which include representative photographs of two study subjects, following three weeks of cream application the upper part of the right forearm appeared much whiter than prior to cream application.

The LIP cream is more efficient in skin whitening than the Hydroquinone cream—The effect of the LIP cream in reducing skin pigmentation was compared with that of 2% Hydroquinone. Following 21 days of cream application the pigmentation of the LIP-treated area of study subject No. 1 was reduced by 3.33 units (FIG. 12a blue columns and FIG. 12c blue curve). On the other hand the pigmentation of the untreated area in the same forearm was reduced by 1.13 units (FIG. 12a, light blue columns). On the other hand, following 21 days of treatment using the Hydroquinone cream the pigmentation of the treated area was reduced by only 1 unit (FIG. 12b pink columns and FIG. 12c pink curve). Similar effects were observed in other study subjects as is shown in FIGS. 14a-c. When results from all 12-study subjects were summarized it was found that the average reductions in skin pigmentation were 1.57 units (FIG. 15a, blue curve) and 1.49 (FIG. 15a, pink curve) units in LIP-treated and Hydroquinone-treated forearms, respectively. Moreover, when the reductions in skin pigmentations were normalized to the initial skin pigmentation the average decreases in skin pigmentations were 4.3% (FIG. 15b, blue curve) and 3.8% (FIG. 15b, pink curve) for the LIP-treated and Hydroquinone-treated forearms, respectively.

Altogether, these results demonstrate that the LIP cream is highly efficient in reducing skin pigmentation. Moreover, these results suggest that the relative whitening effect of the LIP cream is higher than the relative whitening effect observed using the 2% Hydroquinone cream.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences iden-

REFERENCES

1. Alaluf S, Heath A, Carter N, Atkins D, Mahalingam H, Barret K, Kolb R, Smit N. (2001). Variation in melanin content and composition in Type V and VI photoexposed and photoprotected human skin: the dominant role of DHI. Pigment Cell Res. 14: 337-347.
2. Cooksey C J, Garratt P J, Land E J, Pavel S, Ramsden C A, Riley P A, Smit N P M. (1997). Evidence of the indirect formation of the catecholic intermediate substrate responsible for the autoactivation kinetics of tyrosinase. J. Biol. Chem. 272: 26226-35.
3. Farrell, R. L., Murtagh, K. E., Tien, M., Mozuch, M. D., Kirk, T. K. (1989). Physical and enzymatic properties of lignin peroxidase isoenzymes from *Phanerochaete chrysosporium*. Enzyme. Microb. Technol. 11: 322-328.
4. Ghose, T. K. (1987). Measurements of cellulase activities. Pure Appl. Chem. 59: 257-268.
5. Ritch, T. G., Nipper, V. J., Akileswaran, L., Smith, A. J., Pribnow, D. G., Gold, M. H. (1991). Lignin peroxidase from the basidiomycetes *Phanerochaete chrysosporium* is synthesized as a preproenzyme. Gene 107: 119-126.
6. Tien, M., and Kirk, T. K. (1984). Lignin degrading enzyme from *Phanerochaete chrysosporium*. Purification, characterization and catalytic properties of a unique $H_2O_2$-requiring oxygenase. Proc. Natl. Acad. Sci. USA. 81: 2280-2284.
7. Kuan, I. C. and Tien, M. (1989). Phosphorylation of lignin peroxidase from *Phanerochaete chrysosporium*. J. Biol. Chem. 264: 20350-20355.
8. Dosoretz, C. G. and Grethlein, H. E. (1991). Physiological aspects of the regulation of extracellular enzymes of *Phanerochaete chrysosporium*. Appl. Biochem. Biotechnol. 28: 253-265.
9. Stewart, P., Kersten, P., Van den Wymelenberg, A., Gaskell, J., Cullen, D. (1992). Lignin peroxidase gene family of *Phanerochaete chrysosporium*: complex regulation by carbon and nitrogen limitation and identification of a second dimorphic chromosome. J. Bacteriol. 174: 5036-5042.
10. van der Woude, M. W., Boominathan, K., Reddy, C. A. (1993). Nitrogen regulation of lignin peroxidase and manganese-dependent peroxidase production is independent of carbon and manganese regulation in *Phanerochaete chrysosporium*. Arch. Microbiol. 160: 1-4.
11. Dosoretz, C. G., Chen, H. C., Grethlein, H. E. (1990). Effect of oxygenation conditions on submerged cultures of *Phanerochaete chrysosporium*. Appl. Microbiol. Biotechnol. 34: 131-137.
12. Faison, B. D. and Kirk, T. K. (1985). Factors involved in the regulation of a ligninase activity in *Phanerochaete chrysosporium*. Appl. Environ. Microbiol. 49: 251-254.
13. Leisola, M., Ulmer, D., Fiechter, A. (1983). Problem of oxygen transfer during degragation of lignin by *Phanerochaete chrysosporium*. Eur. J. Appl. Microbiol. Biotechnol. 17: 113-116.
14. Michel, F. C., Grulcke, E. A., Reddy, C. A. (1992). Determination of the respiration kinetics for mycelial pellets of *Phanerochaete chrysosporium*. Appl. Environ. Microbiol. 58: 1740-1745.
15. Popp, J. L., Kalyanaraman, B., Kirk, T. K. (1990). Lignin peroxidase oxidation of $Mn^{2+}$ in the presence of veratryl alcohol, malonic or oxalic acid, and oxygen. Biochemistry 29: 10475-10480.
16. Rothschild, N., Levkowitz, A., Hadar, Y., Dosoretz, C. (1999). Manganese deficiency can replace high oxygen levles needed for lignin peroxidase formation by *Phanerochaete chrysosporium*. Appl. Environ. Microbiol. 65: 483-8.

What is claimed is:

1. A cosmetic composition for lightening a skin region or hair of a subject comprising at least one type of a lignin peroxidase enzyme at a concentration of 1 to 100 U/gr and a cosmetically acceptable carrier which includes transcutol, butylene glycol and/or alkanol amines.

2. The cosmetic composition of claim 1, wherein said lignin peroxidase is isoenzyme H1 or a dephosphorylated form of isoenzyme H2.

3. The cosmetic composition of claim 1, further comprising an oxidizing mediator.

4. The cosmetic composition of claim 1, wherein said cosmetic composition is a topical cream.

5. The cosmetic composition of claim 2, wherein said isoenzyme H1 and said dephosphorylated form of isoenzyme H2 are purified by chromatography.

6. The cosmetic composition of claim 3, wherein said oxidizing mediator is veratryl alcohol.

7. The cosmetic composition of claim 6, wherein said veratryl alcohol is provided at a concentration of at least 0.05% (w/w).

8. A kit for lightening a skin region or hair comprising a first container including a lignin peroxidase enzyme at a concentration of 1 to 100 U/gr, and a second container including an oxidizing activator, wherein said first and/or second container(s) further include transcutol, butylene glycol and/or alkanol amines.

9. The kit of claim 8, wherein said first container further comprises an oxidizing mediator.

10. The kit of claim 8, wherein said lignin peroxidase is isoenzyme H1 or a dephosphorylated form of isoenzyme H2.

11. The kit of claim 8, wherein said oxidizing activator is hydrogen peroxide.

12. The kit of claim 9, wherein said oxidizing mediator is veratryl alcohol.

13. The kit of claim 10, wherein said wherein said isoenzyme H1 and said dephosphorylated form of isoenzyme H2 are purified by chromatography.

14. The kit of claim 11, wherein said hydrogen peroxide is provided at a concentration of at least 0.005% (w/w).

15. The kit of claim 12, wherein said is veratryl alcohol is provided in a concentration of at least 0.05% (w/w).

* * * * *